(12) United States Patent
Tutungi et al.

(10) Patent No.: US 10,653,861 B2
(45) Date of Patent: May 19, 2020

(54) ELONGATE STEERABLE DEVICES FOR INSERTION INTO A SUBJECTS BODY

(71) Applicant: INTELLIMEDICAL TECHNOLOGIES PTY LTD, South Jordan, UT (US)

(72) Inventors: Elli Tutungi, Glen Waverly (AU); Brody C. Payne, Clifton Hill (AU); Aubrey Almeida, Balwyn (AU); Geoffrey William Rogers, Fitzroy (AU)

(73) Assignee: Intellimedical Technologies Pty. Ltd., South Jordan, UT (US)

(*) Notice: Subject to any disclaimer, the term of this patent is extended or adjusted under 35 U.S.C. 154(b) by 0 days.

(21) Appl. No.: 15/307,984

(22) PCT Filed: Apr. 30, 2015

(86) PCT No.: PCT/AU2015/000253
§ 371 (c)(1),
(2) Date: Oct. 31, 2016

(87) PCT Pub. No.: WO2015/164912
PCT Pub. Date: Nov. 5, 2015

(65) Prior Publication Data
US 2017/0165456 A1 Jun. 15, 2017

Related U.S. Application Data

(60) Provisional application No. 61/988,001, filed on May 2, 2014.

(51) Int. Cl.
*A61M 25/01* (2006.01)
*A61M 25/09* (2006.01)
(Continued)

(52) U.S. Cl.
CPC ....... *A61M 25/0147* (2013.01); *A61B 1/0052* (2013.01); *A61B 1/0057* (2013.01);
(Continued)

(58) Field of Classification Search
CPC ............ A61B 1/0052; A61B 2034/301; A61B 1/0057; A61M 25/09041; A61M 25/0147;
(Continued)

(56) References Cited

U.S. PATENT DOCUMENTS

| 3,605,725 A | 9/1971 | Bentov |
| 5,108,368 A | 4/1992 | Hammerslag et al. |

(Continued)

FOREIGN PATENT DOCUMENTS

| DE | 19933278 | 1/2001 |
| WO | 199411057 | 5/1994 |

(Continued)

*Primary Examiner* — Emily L Schmidt
(74) *Attorney, Agent, or Firm* — Stoel Rives LLP

(57) ABSTRACT

Elongate, steerable devices for insertion into a subject's body, including very narrow (small diameter) devices that may be configured as steerable catheters and guidewires for use in interventional cardiology and neuroradiology. Also described are methods of making and using these devices, and controllers for controlling these steerable devices. These steerable devices may have a bendable distal region, a plurality of tendons each attached to the distal bendable region and extending from the distal bendable region to a proximal handle region with a plurality of axial translation regions. The axial translation regions may be arranged along an outer surface of the proximal handle region and each axial translation region may be coupled to a tendon for bending the distal region. The axial translation regions may be elastically connected to each other, and configured to translate the tendon and thereby steer the distal bendable region.

17 Claims, 30 Drawing Sheets

(51) Int. Cl.
*A61B 1/005* (2006.01)
*A61M 25/00* (2006.01)
*A61B 34/30* (2016.01)
*A61B 17/00* (2006.01)

(52) U.S. Cl.
CPC ...... *A61M 25/005* (2013.01); *A61M 25/0009* (2013.01); *A61M 25/0108* (2013.01); *A61M 25/0127* (2013.01); *A61M 25/0133* (2013.01); *A61M 25/09041* (2013.01); *A61B 2017/00323* (2013.01); *A61B 2034/301* (2016.02); *A61M 2025/0161* (2013.01); *A61M 2025/09166* (2013.01); *A61M 2205/0216* (2013.01)

(58) Field of Classification Search
CPC ...... A61M 25/0136; A61M 2025/0161; A61M 2025/09116; A61M 25/0133; A61M 25/09025; B25J 15/0286; B25J 9/104
See application file for complete search history.

(56) References Cited

U.S. PATENT DOCUMENTS

| | | | |
|---|---|---|---|
| 5,297,443 A | 3/1994 | Wentz | |
| 5,480,382 A | 1/1996 | Hammerslag et al. | |
| 5,507,995 A | 4/1996 | Schweich et al. | |
| 5,673,707 A | 10/1997 | Chandrasekaran | |
| 5,676,653 A | 10/1997 | Taylor et al. | |
| 5,704,898 A | 1/1998 | Kokish | |
| 6,236,876 B1 | 5/2001 | Gruner et al. | |
| 6,475,187 B1 | 11/2002 | Gerberding | |
| 6,712,807 B2 | 3/2004 | Stivland et al. | |
| 7,449,002 B1 | 11/2008 | Wenstad | |
| 7,867,176 B2 | 1/2011 | Wu et al. | |
| 7,914,445 B2 | 3/2011 | Smith et al. | |
| 7,914,466 B2 | 3/2011 | Davis et al. | |
| 8,353,850 B2 | 1/2013 | Ressemann et al. | |
| 8,403,833 B2 | 3/2013 | Umemoto | |
| 8,444,637 B2 | 5/2013 | Podmore et al. | |
| 8,500,733 B2 | 8/2013 | Watson | |
| 2006/0052664 A1* | 3/2006 | Julian | A61B 1/0053 600/146 |
| 2008/0027285 A1 | 1/2008 | Yasunaga | |
| 2008/0058722 A1 | 3/2008 | Von Oepen et al. | |
| 2008/0097465 A1 | 4/2008 | Rollins et al. | |
| 2008/0172037 A1 | 7/2008 | Huang et al. | |
| 2009/0012465 A1 | 1/2009 | Latini | |
| 2009/0234280 A1 | 9/2009 | Tah et al. | |
| 2009/0248042 A1 | 10/2009 | Kirschenman | |
| 2010/0099952 A1 | 4/2010 | Adams | |
| 2010/0280320 A1* | 11/2010 | Alvarez | A61B 17/00234 600/146 |
| 2010/0331820 A1 | 12/2010 | Prisco et al. | |
| 2011/0015484 A1 | 1/2011 | Alvarez et al. | |
| 2011/0021984 A1 | 1/2011 | Kirschenman et al. | |
| 2011/0130718 A1 | 6/2011 | Kidd et al. | |
| 2011/0295242 A1 | 12/2011 | Spivey et al. | |
| 2012/0065481 A1 | 3/2012 | Hunter et al. | |
| 2012/0123395 A1 | 5/2012 | Stoy et al. | |
| 2012/0165812 A1 | 6/2012 | Christian | |
| 2012/0179167 A1* | 7/2012 | Wenderow | A61B 34/30 606/130 |
| 2012/0232476 A1 | 9/2012 | Bhat et al. | |
| 2012/0238952 A1 | 9/2012 | Mitchell et al. | |
| 2013/0041314 A1 | 2/2013 | Dillon | |
| 2013/0072904 A1 | 3/2013 | Musbach et al. | |
| 2013/0267913 A1 | 10/2013 | Northrop | |
| 2014/0052109 A1 | 2/2014 | Organ et al. | |

FOREIGN PATENT DOCUMENTS

| | | |
|---|---|---|
| WO | 2004068947 | 8/2004 |
| WO | WO2005000105 A2 | 1/2005 |
| WO | WO2007035471 A2 | 3/2007 |
| WO | WO2008085167 A1 | 7/2008 |
| WO | 2009127236 | 10/2009 |
| WO | WO2009120944 A2 | 10/2009 |
| WO | WO2009125744 A1 | 10/2009 |
| WO | WO2009137410 A1 | 11/2009 |
| WO | WO2010026495 A2 | 3/2010 |
| WO | WO2012018435 A1 | 2/2012 |
| WO | WO2013096610 A1 | 6/2013 |

* cited by examiner

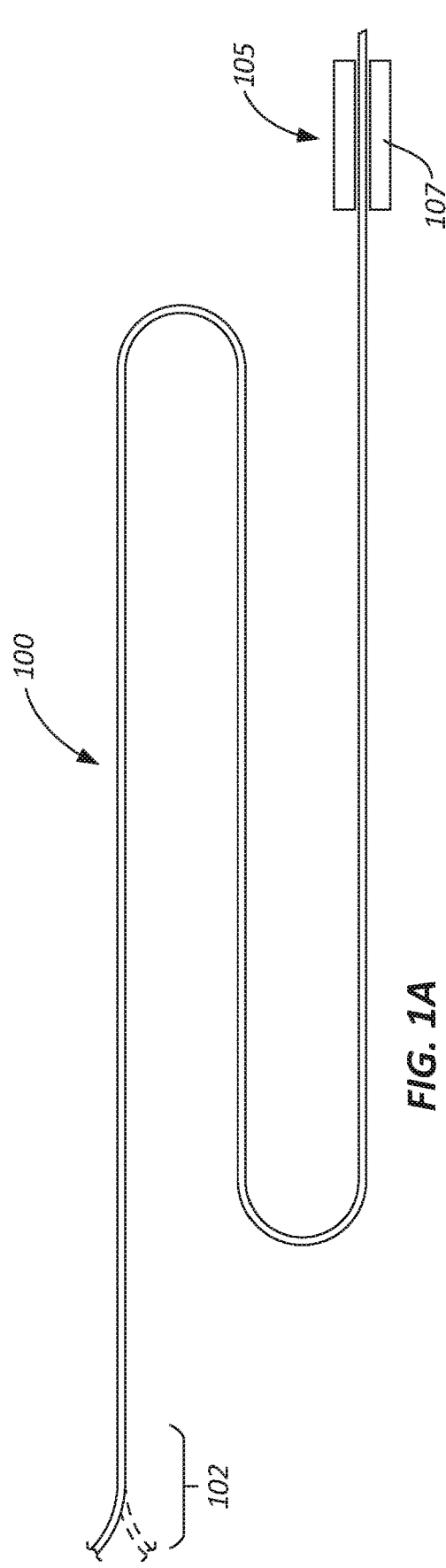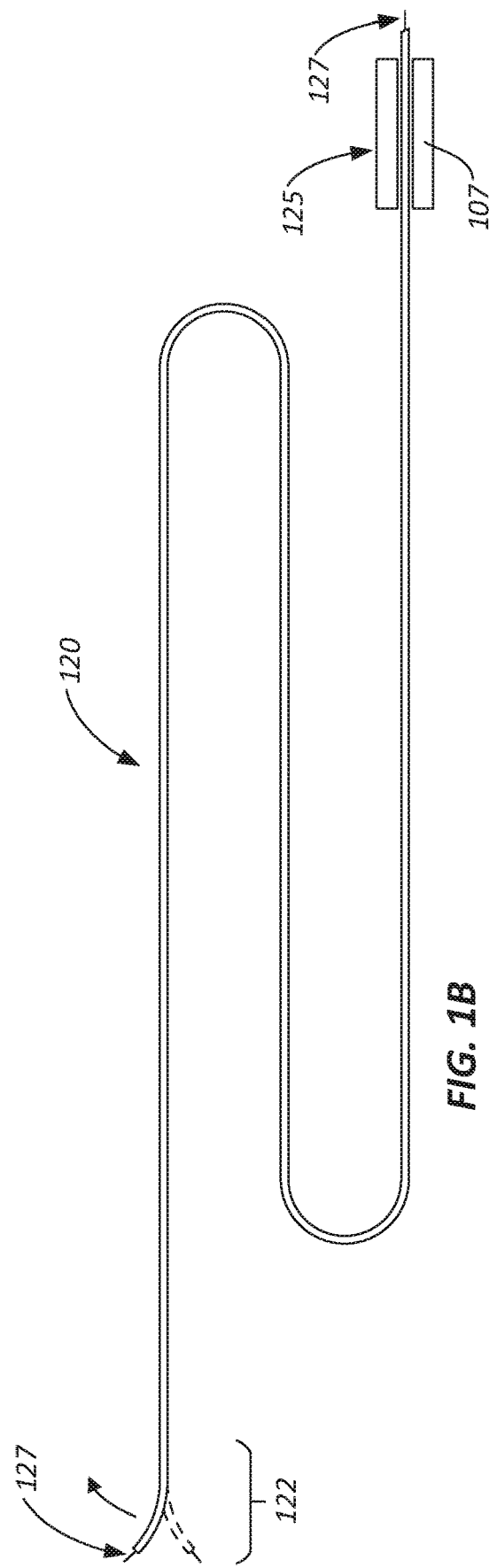

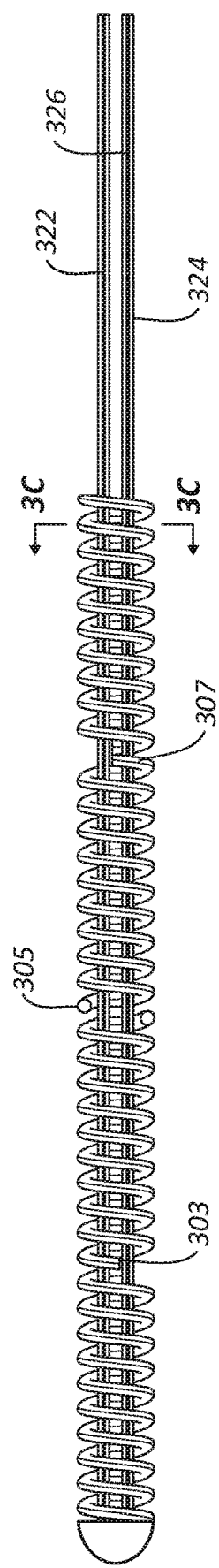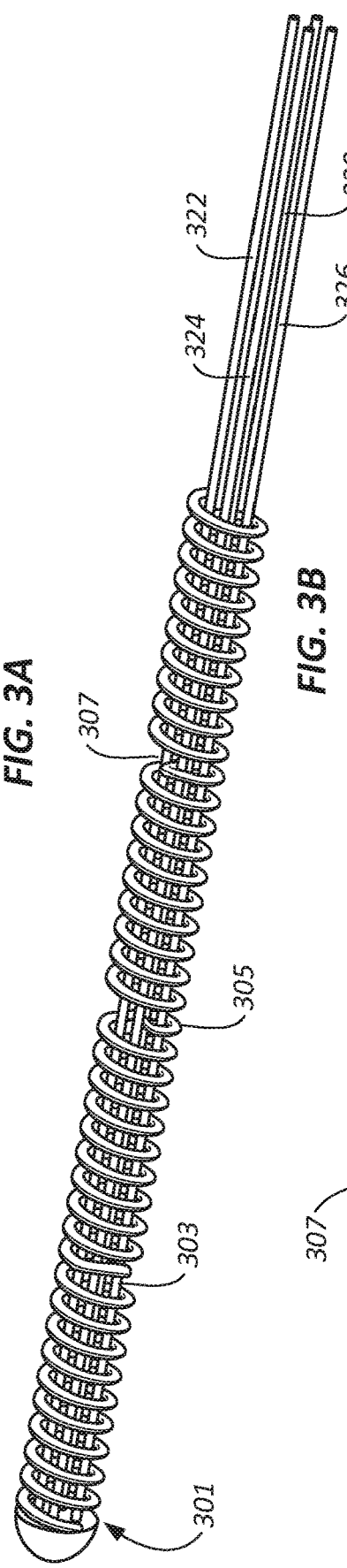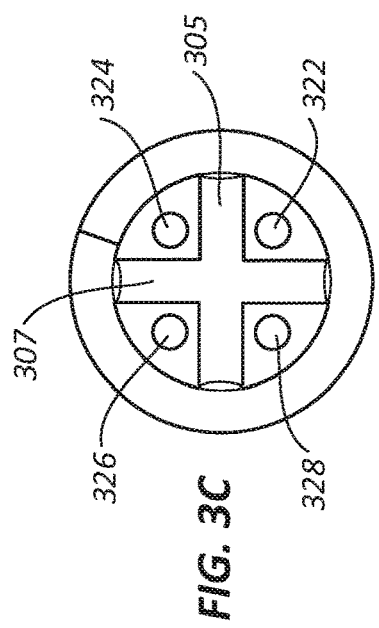
FIG. 3A
FIG. 3B
FIG. 3C

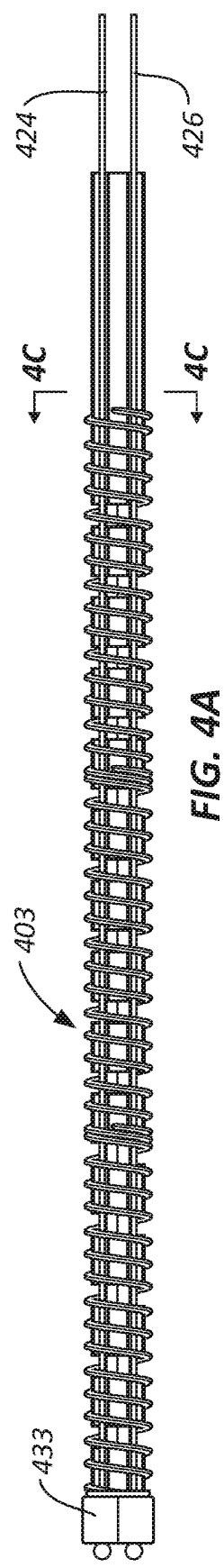
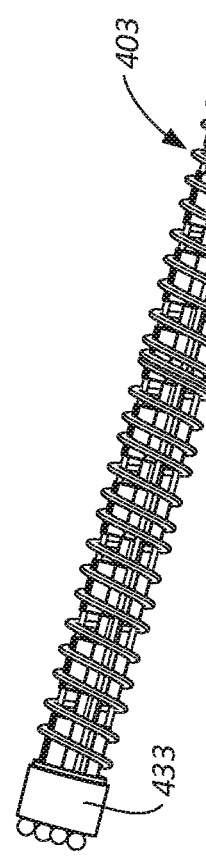
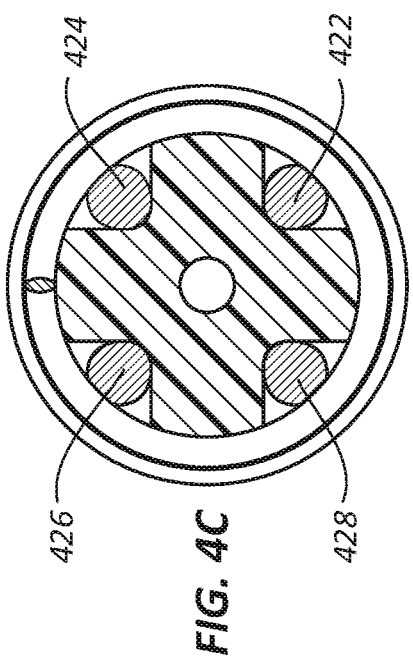
FIG. 4A
FIG. 4B
FIG. 4C

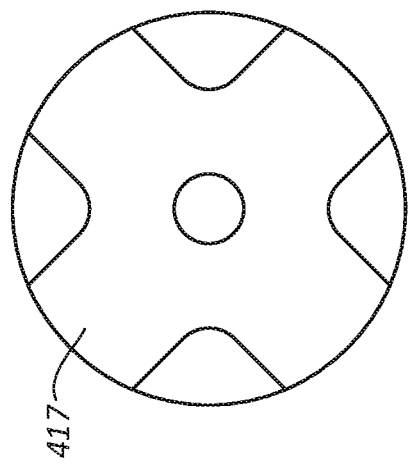
FIG 4E
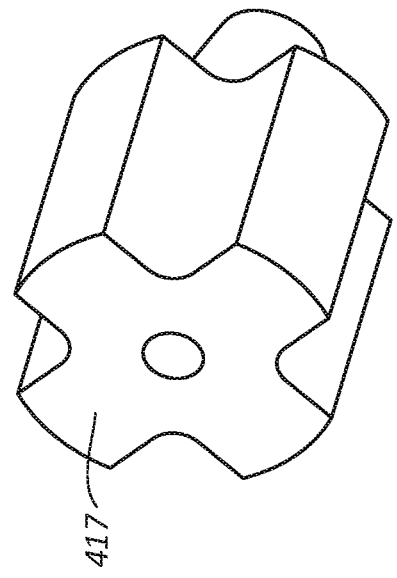
FIG 4D
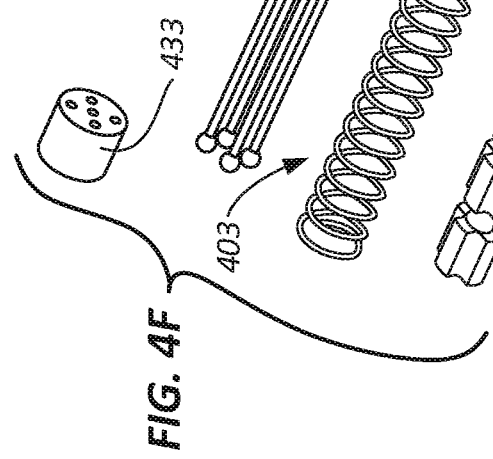
FIG. 4F
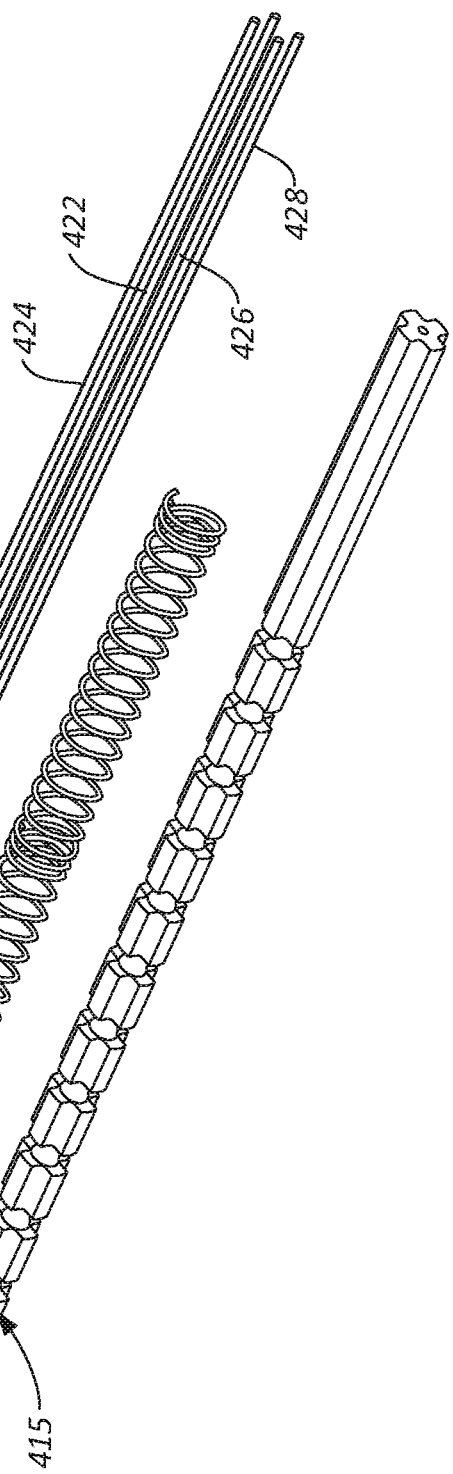

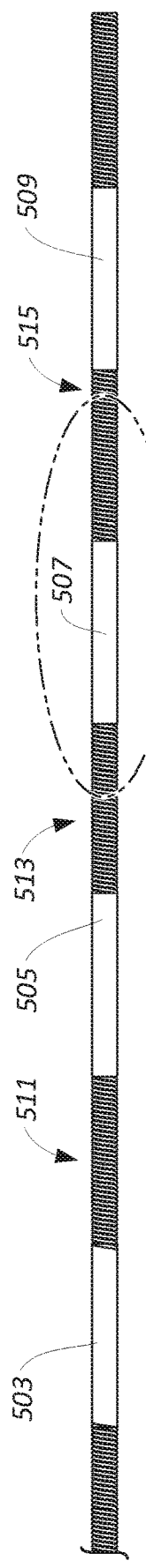
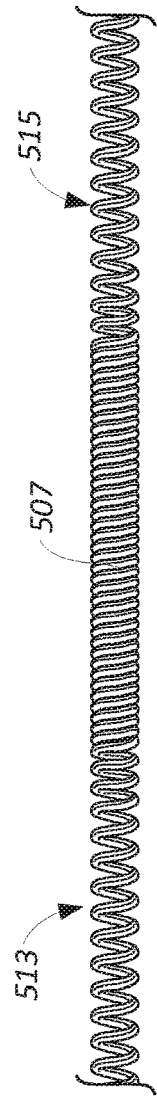
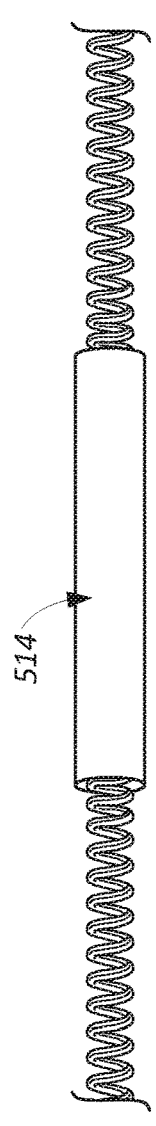
FIG. 5A
FIG. 5B
FIG. 5C
FIG. 5D
FIG. 5E

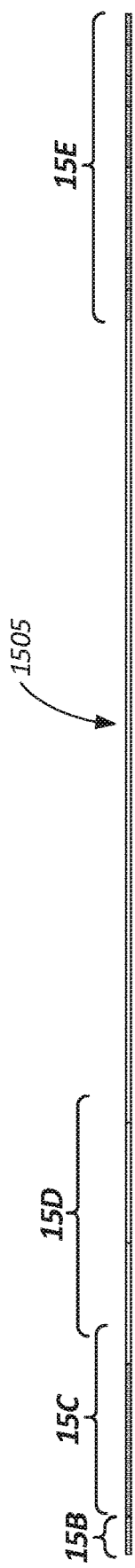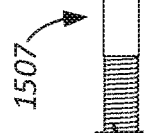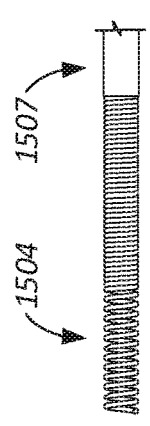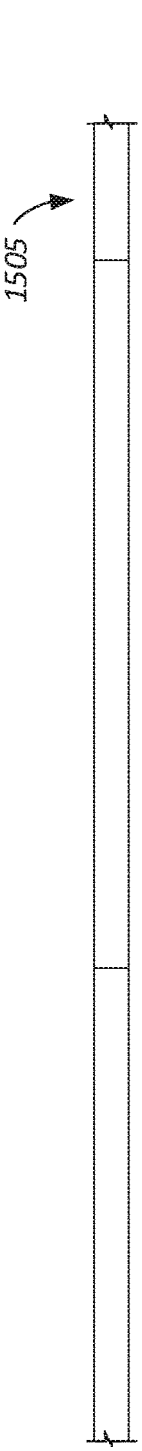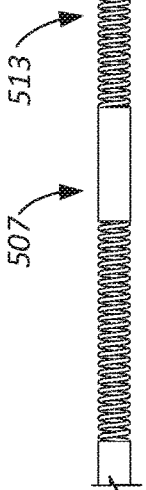
FIG. 15A
FIG. 15B
FIG. 15C
FIG. 15D
FIG. 15E

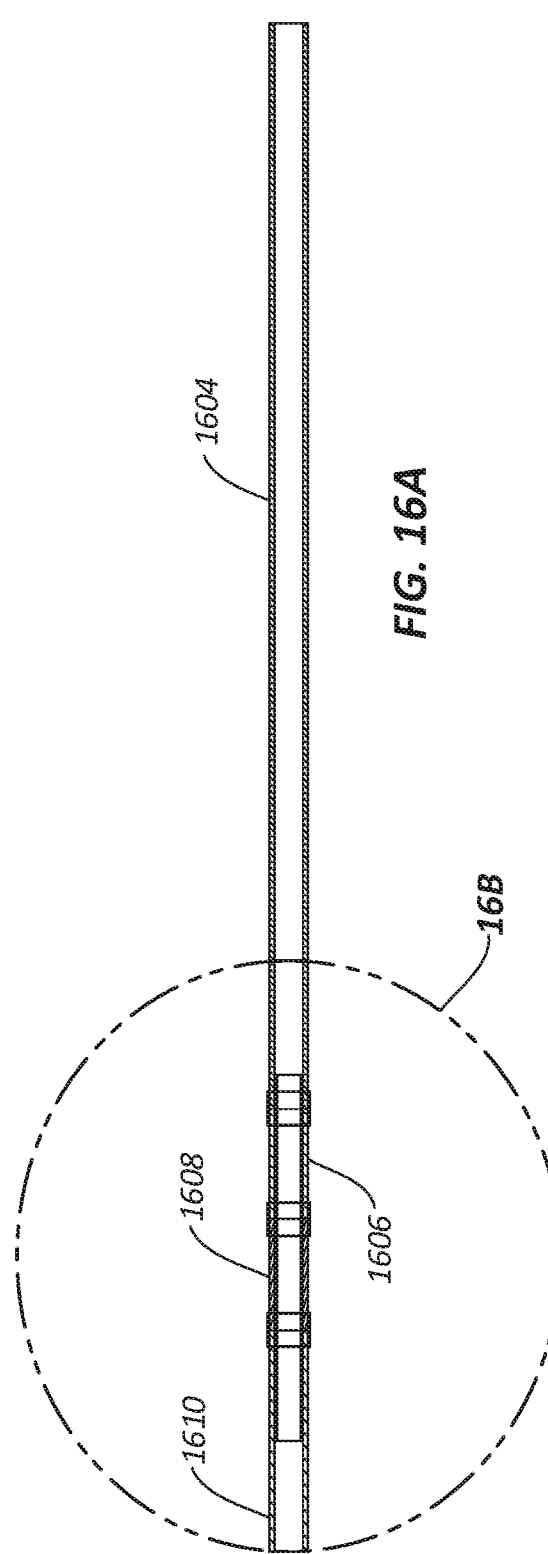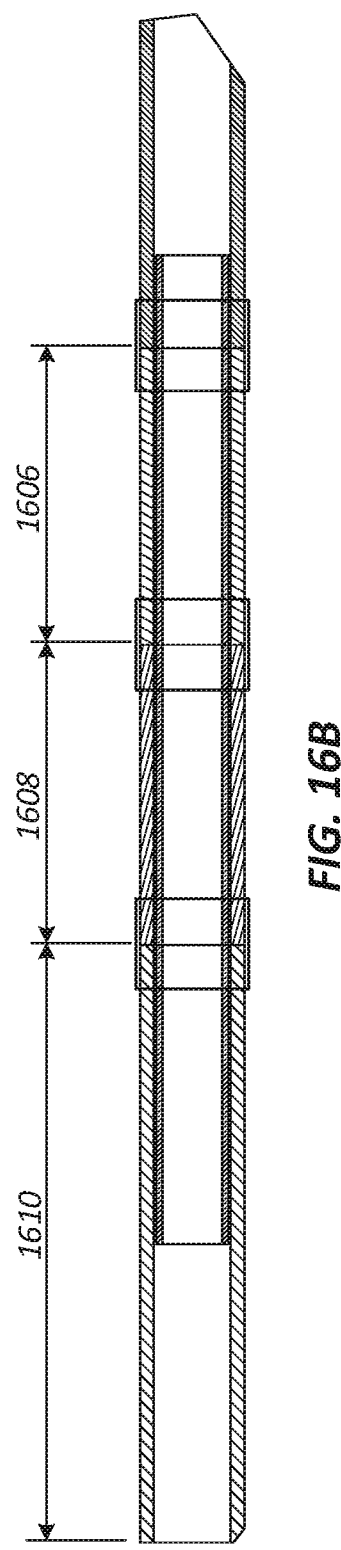

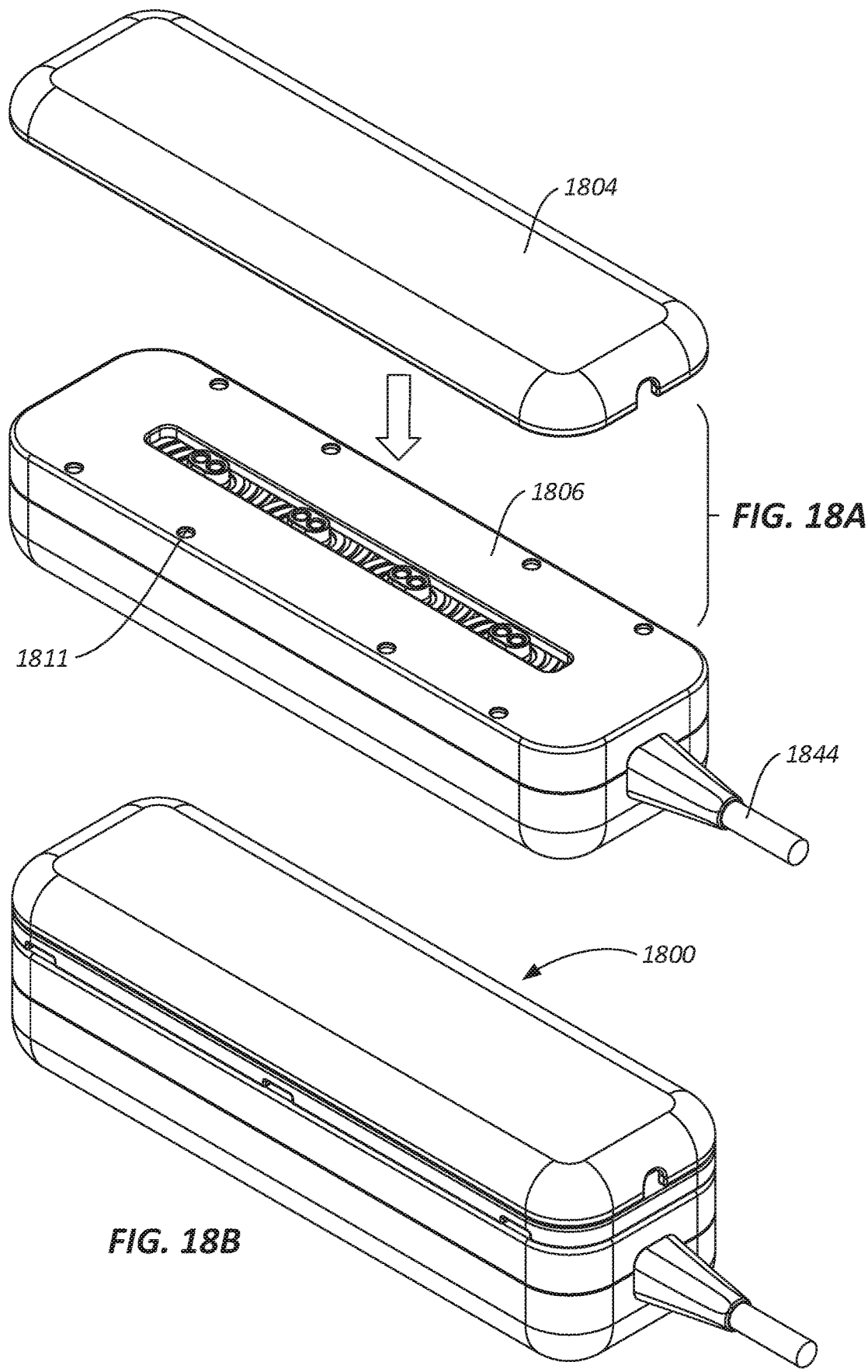

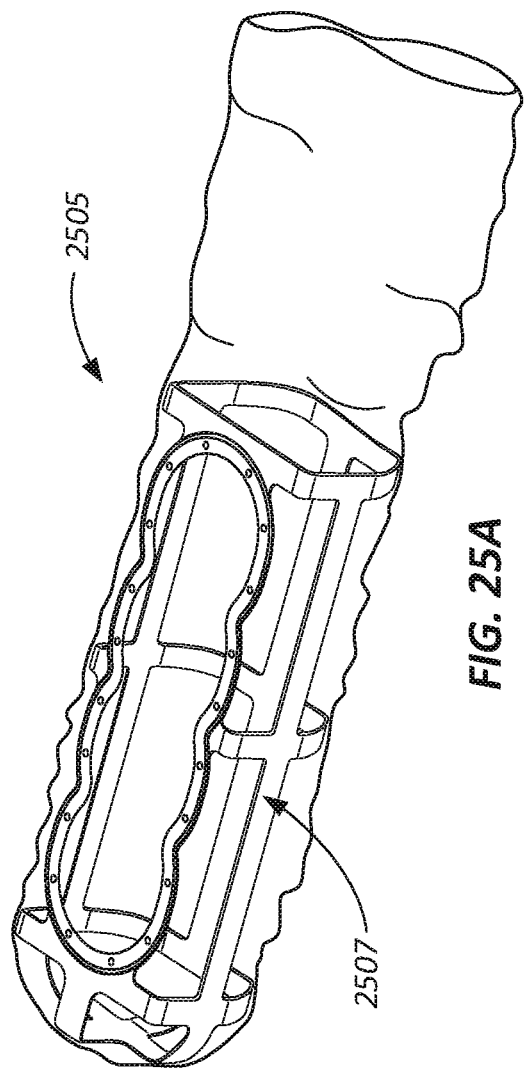
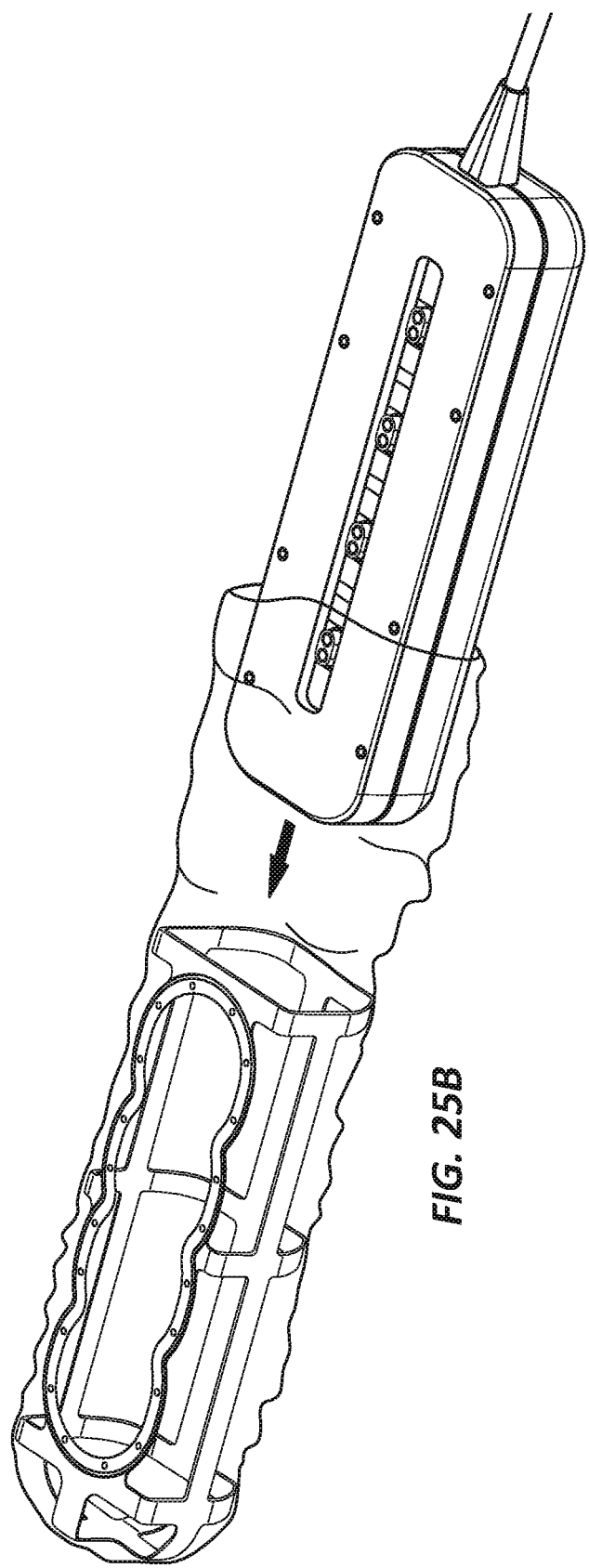
FIG. 25A
FIG. 25B

US 10,653,861 B2

ELONGATE STEERABLE DEVICES FOR INSERTION INTO A SUBJECTS BODY

CROSS REFERENCE TO RELATED APPLICATIONS

This patent application claims priority to U.S. provisional patent application No. 61/988,001, field on May 2, 2014 and titled "ELONGATE STEERABLE DEVICES FOR INSERTION INTO A SUBJECT'S BODY".

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are elongate, steerable and insertable devices having extremely low profiles (e.g., thin), as well as devices (controllers) for steering them. For example, described herein are steerable guidewires and catheters that may be used in interventional cardiology and neuroradiology, and may be robotically controlled.

BACKGROUND

Steerable guidewires and catheters that have been previously described primarily include one or more mechanical tension wires housed within a lumen of the guidewire/catheter, which can be selectively tensioned from the proximal end to cause the distal tip to deflect/bend. However, due to the complex construction required to form these devices, most have outer diameters of greater than 5 mm, with the smallest presently around 2 mm. These devices are typically used in electrophysiology and other applications where the vessels to be navigated are relatively large, but are not suitable for use in interventional cardiology (IC) and neuroradiology (NR) procedures.

For example, a (non-steerable) guidewire suitable for use in IC and NR procedures is the 1 F (0.014" or 0.36 mm) guidewire. The corresponding catheter for use with these devices has an inner diameter slightly larger than 1 F, such that it passes over the 1 F guidewire. The sizes of IC and NR guidewires and catheters are considerably smaller than existing steerable devices, as they need to navigate much smaller vessels (as small as 0.5 mm in diameter).

Thus, there is a need for extremely low-profile apparatuses (e.g., micro-guidewires and micro-catheters) that are steerable in vivo. Described herein are apparatuses (e.g., devices and systems) and methods of making and operating them, which address these needs. Any of the apparatuses described herein may be robotically, automatically and/or manually steerable.

The steerable apparatuses, controllers and methods of making and using them described herein may include a number of key features that allow a reduction in the diameter of the apparatuses without compromising functionality.

SUMMARY OF THE DISCLOSURE

The present invention relates generally to elongate, thin and steerable apparatuses (devices and methods) for insertion into a human body, and methods of making and using them. In particular, the elongate, steerable devices described herein typically include an elongate body having at least one inner lumen, one, or more preferably multiple, tendons coupled to a distal bending region (e.g., the distal tip region) at a distal end and coupled to a proximal axial translation region at a proximal end.

In general, the proximal end may be configured to have multiple, in-line axial translation regions that each couple to a pull-wire or tendon so that axially moving the axial translation region relative to other regions of the device (e.g., pushing or pulling it longitudinally in the direction that the apparatus extends) may result in moving the pull-wire or tendon and bending the bendable distal region. The in-line axial translation regions may be connected to each other, e.g., elastically connected to each other via a spring or stretchable/compressible material.

Any of the devices described herein may be configured as a guidewire or catheter. For example, a catheter may include an inner lumen extending all or most of the length of the device through which a material or structure (e.g., guidewire) may be passed. A steerable guidewire as described herein may not include this additional lumen.

In general, the elongate body of the device may be formed of a coil or multiple coils, longitudinally arranged. The elongate body is generally flexible and/or bendable, so that it can be used to navigate through a body, including through a vascular region of a body. One or more distal regions of the elongate body may be steerable regions, including, but not limited to, the distal end of the apparatus. In some variations a device may include multiple steerable regions. The steerable region(s) may have an increased flexibility/bending. One or more, and typically 2, 3, 4, 5 or more tendons may be attached to pull and/or push the bending steerable region. The distal end of each tendon is attached at or near the steerable region (e.g., at a distal end of the steerable region) and the proximal end of each tendon is typically attached to a proximal axial translation region. The tendon is typically held within the elongate body. In particular, the tendons, particularly near the steerable distal region(s), may be held at or near the radially outer region of the elongate body, and prevented from interacting with each other by a spacer or inner member.

In general, the proximal end of the device may be configured as a handle including a number of axial translation regions corresponding to the number of tendons. The axial translation regions may be located annularly or partially annularly around an outer surface of the proximal handle region and arranged in-line. The axial translation regions are configured to be axially displaced (distally and/or proximally) relative to the elongate body and/or each other; moving an axial translation region will result in moving (e.g., pushing or pulling) the tendon that is attached thereto, and thereby exert or release a bending force on the distal steerable region. In variations in which a plurality of axial translation regions are present, they may be arranged longitudinally adjacent to each other, though with intervening regions (e.g., compressible/expandable regions) connecting them. Thus, they may be elastically connected to each other. Each of the annular outer surface regions that are adapted as axial translation regions may be easily and separately clamped/unclamped by a controller holding the outer surface of the proximal end of the device. Thus, a structure may be easily passed over the device (e.g., slid over the device) or into the device (passed through an inner lumen) without requiring an involved detaching/reattaching procedure. In addition, the controller (examples of which are also provided herein) may be relatively simple and easy to use. Alternatively, the devices may be manually controlled by manipulating the axial translation regions directly.

For example, described herein are elongate steerable devices for insertion into a subject's body. An elongate steerable device may extend from a bendable distal tip region to a proximal handle region in a proximal to distal direction, and may include: a plurality of tendons, wherein each tendon of the plurality of tendons is attached to the distal tip region and extends from the distal tip region to the proximal handle region; a plurality of axial translation regions arranged along an outer surface of the proximal handle region, wherein each axial translation region of the plurality of axial translation regions is coupled to a tendon of the plurality of tendons; wherein each axial translation region is configured to move in a distal to proximal line to axially translate the tendon coupled to the axial translation region and thereby deflect the distal tip.

Each axial translation region is configured to move in a proximal to distal line relative to the proximal and distal length of the device. Thus, each axial translation region may move back and forth (e.g., towards the proximal end and away from the distal end, or towards the distal end and away from the proximal end), in longitudinal movement to bend the distal tip region. The proximal to distal line described herein may be a straight line or a non-straight (e.g., curved) line.

As described in greater detail below, the axial translation regions may be elastically connected to each other, and/or they may be connected to a central core/slider.

Another example of an elongate steerable device for insertion into a subject's body, in which the device extends from a bendable distal tip region to a proximal handle region in a proximal to distal direction, includes: a first tendon extending within the device from the distal tip region of the device to the proximal handle region of the device; a second tendon extending within the device from the distal tip region of the device to the proximal handle region of the device; a first axial translation region on an outer surface of the proximal handle region, wherein the first axial translation region is coupled to the first tendon and configured to move in the distal to proximal direction to axially translate the first tendon and thereby deflect the distal tip in a first direction; and a second axial translation region on the outer surface of the proximal handle region, wherein the second axial translation region is coupled to the second tendon and configured to move in the distal to proximal direction to axially translate the second tendon and thereby deflect the distal tip in a second direction; wherein the first and second axial translation regions are elastically connected to each other.

Another example of an elongate steerable device for insertion into a subject's body (the device extending in a proximal to distal direction), includes: an elongate body having a bendable distal tip region, an intermediate region and a proximal handle region; a first tendon extending within the elongate body of the device from the distal tip region to the proximal handle region; a second tendon extending within the elongate body of the device from the distal tip region to the proximal handle region; a first axial translation region on an outer surface of the proximal handle region of the elongate body, wherein the first axial translation region is coupled to the first tendon; and a second axial translation region on the outer surface of the proximal handle region, wherein the second axial translation region is coupled to the second tendon; wherein the first and second axial translation regions are elastically connected to each other. In some variations, the apparatus includes a plurality of translation regions (axial translation regions) that are not connected to each other. For example, the translation regions may comprise a plurality of individual sliders moving in one or more channels or on one or more guide rails in the proximal handle.

As mentioned, any of these devices may be configured as a guidewire or as a catheter (e.g., having a central lumen extending therethrough).

In general, the axial translation regions (e.g., the first and second axial translation regions) may be adjacently arranged along the outer surface of the proximal handle region. The axial translation regions may comprise cylindrical regions that are adjacently arranged along the outer surface of the proximal handle region (including forming the outer surface of the device in the proximal handle region).

In general, a tendon may be a wire (e.g., pull wire/push wire), rod (e.g., pull rod/push rod), strand, fiber, etc., or the like. The tendons may be attached to the distal bending (e.g., tip) region at radially offset attachment sites. In particular, the tendons ("tension wires") may be multi-filament (e.g. yarn or braid) tension wires. Tendons may also be mono-filaments (e.g. steel or Nitinol wire). For example, a multi-filament tendon may comprise a yarn with an OD of approximately 0.04 mm, comprising, e.g., five individual fibers each measuring about 0.01 mm.

The axial translation regions may be configured to move in the distal to proximal direction to axially translate the tendon that they are connected to and thereby deflect the distal tip. For example, translating a first axial translation region distally or proximally may move the first tendon and bend the distal steerable region in a first direction; a second axial translation region may be configured to move in the distal to proximal direction to axially translate a second tendon and thereby deflect the distal tip in a second direction. The axial translation regions may also move in the proximal to distal direction (e.g., to restore the position). In some variations, the actuator may move the axial translation regions in the proximal to distal direction (e.g. "pushing" the tendon) to transmit a compressive load to deflect the tip; actuating the axial translation region distally to proximally may "pull" the tendon to deflect the tip. In some variations the apparatus may be adapted so that only pulling (non-compressive) forces are applied by the actuator; in other variations the apparatus may be adapted to apply both compressive and pulling (extension) forces; in still other variations only compressive forces may be applied. Either or both the steerable device and/or the actuator may be configured to operate in either or both compressive and/or extension of the tendons.

The elongate body may generally be formed as a coil (e.g., helical coil), and may generally include the bendable distal tip region, an intermediate region and the proximal handle region. The elongate body may have different flexibility/bendability along different regions of the length. For example, the elongate body may comprise a coil having different pitches and/or pre-tensions along the length of the elongate body. In particular, the handle region may include regions that are relatively rigid (e.g., axial translation regions) separated by flexible, elastic, or movable regions. These flexible, elastic, and/or axially expandable/compressible regions may connect adjacent axial translation regions. For example, the elongate body may include a bendable distal tip region, an intermediate region and a proximal handle region, wherein the elongate body comprises a coil having a plurality of different pitches along the length of the elongate body; the handle may include axial translation regions formed of tight pitch (relatively stiff) regions that may be fused or glued together, separated by regions having a more flexible (expandable/compressible) pitch and/or material.

Also described herein are methods of using these devices. For example, a method of steering an elongate device having a plurality of tendons, wherein each tendon is coupled at a distal end of the device to a distal tip region and each tendon is coupled to a separate axial translation region at a proximal end of the device, and wherein the axial translation regions are arranged in a proximal to distal line along a proximal handle region of the device and the axial translation regions are elastically connected to each other, may include: separately holding at least a first one and a second one of the axial translation regions; and sliding the first one of the axial translation regions proximally or distally relative to the second one of the axial translation regions to increase or decrease the distance between the first one and the second one, axially translating the tendon that is coupled with the first one to deflect the distal tip region.

In general, the method may also include inserting the device into a subject's body. Separately holding may comprise frictionally securing each of the axial translation regions to a separate gripper of an actuator.

The method may also include holding a portion of the device that is distal or proximal to the proximal handle region while sliding a first one of the axial translation regions so that the first one of the axial translation regions slides relative to the portion of the device that is distal, proximal or distal and proximal to the proximal handle region. Separately holding may include holding the first one of the axial translation regions in a first grip and holding the second one of the axial translation regions in a second grip. In some cases, separately holding each of the axial translation regions comprises holding each of the axial translation regions in separate frictional grips that are independently movable relative to each other. Separately holding each of the axial translation regions may include holding a portion of the device that is distal to the proximal handle region and/or a portion of the device that is proximal to the axial translation regions.

A method of steering an elongate device having a plurality of tendons, wherein each tendon is coupled at a distal end of the device to a distal tip region and each tendon is coupled to separate axial translation regions at a proximal end of the device, and wherein the axial translation regions are arranged in a proximal to distal line along a proximal handle region of the device and the axial translation regions are elastically connected to each other, may include: frictionally securing each of the axial translation regions to a separate gripper of an actuator; and holding a portion of the device that is distal to the proximal handle region while sliding a first one of the axial translation regions proximally or distally relative to a second of the axial translation regions to increase or decrease the distance between the first one and the second one, axially translating the tendon that is coupled with the first one to deflect the distal tip region.

As mentioned above, controllers for controlling the bending of the distal region(s) of the devices described are also included. Controllers may be included along with these devices (e.g., as a system), or separate from the devices. In general, a controller includes one (or more likely a plurality, e.g., 2, 3, 4, 5, 6 or more) pair of discrete gripping surfaces that separately grip the axial translation regions and/or a portion of the device proximal, distal or proximal and distal to the axial translation region(s) so that the axial translation region(s) can be independently actuated to drive bending of the devices. Any of these controllers may be adapted to operate automatically, manually, or both. The elongate steerable devices may be connected to the controller by clamping, gripping or otherwise securing to each of the axial translation regions and/or other regions of the proximal end of the device.

For example, a controller adapted to independently move different axial translation regions of an elongate steerable device for insertion into a subject's body to bend the distal tip of the elongate steerable device may include: two or more pairs of gripping surfaces, wherein the two or more pairs of gripping surfaces are arranged in a line extending proximally to distally, further wherein a distance between the gripping surfaces forming each of the pairs of gripping surfaces is adjustable to allow an elongate body to be clamped between each of the pairs of gripping surfaces; and at least one driver configured to drive translation of the pairs of gripping surfaces, wherein each of the pairs of gripping surfaces is adapted to translate independently of each other.

A controller may also include a stabilizing pair of gripping surfaces located proximally or distally in-line with the two or more pairs of gripping surfaces, wherein the stabilizing pair of gripping surfaces prevents axial translation of the elongate steerable device when translating the one or more pairs of gripping surfaces. In some variations stabilizing gripping surfaces may be located between the axial translation regions.

Although the gripping surfaces described herein include pairs of gripping surfaces that compress axial translation regions (or stabilizing regions of the device) between them, any of these variations may be adapted to use a single gripping surface (e.g., a channel, U-shape, cavity, etc.) or more than 2 gripping surfaces.

The at least one driver may be any appropriate type of driver, including (but not limited) to a mechanical actuator (e.g., motor, etc.), a pneumatic actuator, and an electrical actuator, and the like. The driver may translate in rotation or in linear dimensions. Thus, the pairs of gripping surfaces may be adapted to be translated in the distal to proximal direction, and/or to rotate in a clockwise/counterclockwise direction, etc. For example, at least one of the gipping surfaces of each pair of gripping surfaces is configured as a roller. A driver may be configured to drive translation of multiple pairs of gripping surfaces; for example, a single motor may be adapted to independently drive translation of each of the pairs of gripping surfaces.

A controller may include two or more rails and/or gantries, wherein each of the pairs of gripping surfaces is connected to one of the rails/gantries and is adapted to translate thereon. In some variations, the controller may include one or more rails, wherein each of the pairs of gripping surfaces is connected to one of the rails and is adapted to translate thereon.

In general, a portion (e.g., top portion) of a controller may be hinged, where the hinge is configured to adjust the distance between the gripping surfaces forming each of the pairs of gripping surfaces, allowing the device to be inserted or removed. For example, a controller may include a clamp configured to secure each of the two or more pairs of gripping surfaces onto an elongate body held between each of the pairs of gripping surfaces.

A controller may include a user interface adapted to control translation of each of the pairs of gripping surfaces to steer a distal tip of an elongate device held between each of the pairs of gripping surfaces of the controller. For example, a controller may include buttons, dials, levers, a graphical user interface, etc. to control actuation.

In any of the controllers described, the controller may include at least one limiter configured to limit the translation of the pairs of gripping surfaces (e.g., to less than about 5 mm).

Any of the controllers (control apparatuses) described herein may be configured as multi-part controllers having two, or in some cases more, components that engage with each other. Some of the components may be reusable and some of the components may be single-use or limited reuse (e.g., sterilizable). For example, any of the controller apparatuses described herein may be configured as a controller system to steer the distal tip of an elongate steerable device (e.g., any of the elongate steerable devices described herein), and may include: a cartridge comprising two or more friction grippers arranged in a line extending proximally to distally, wherein each friction gripper is configured to hold a portion of the elongate steerable device, further wherein each friction gripper is independently movable along the line extending proximally to distally; and a driver assembly comprising two or more drive members, wherein each drive member comprises a coupler that is configured to engage one of the friction grippers when the cartridge is coupled with the drive assembly to drive movement in the line extending proximally to distally, further wherein each friction gripper is driven by one or more drive motors within the drive assembly; wherein the cartridge and driver assembly are configured to be removably coupled together through a sterile barrier.

The cartridge may be single-use (e.g., disposable) or reconditioned (e.g., sterilized) after each use. The cartridge may be pre-loaded with the elongate steerable device, and may be separately packaged, e.g., in a sterilized or sterilizable package. The cartridge may include a cover covering the friction grippers. A friction gripper may include any of the pairs of gripping surfaces described herein (or it may include a single gripping surface, e.g., c-shaped gripping surface). Each friction gripper may include a gripping surface and/or clamp and/or lock for clamping onto and securely holding a portion (e.g., a sliding element) of the elongate steerable (e.g., elongate steerable tip) device, such as any of the catheters and/or guidewires described herein. The friction grippers may be held in the cartridge (e.g., within, on and/or in a cartridge housing) so that they are axially slideable in the distal-to-proximal axis (e.g., line extending distally to proximally). For example, the friction grippers may be coupled to one or more rails, channels, etc. and may include bearing surfaces to allow each to move axially within the cartridge. Each of the friction grippers may also include a coupler for coupling with drive member of the driver assembly. In some variations the coupling between the drive member and the friction gripper is done through a sterile barrier, such as a sheet, bag, pouch, etc. The coupler may be a magnetic coupler, which may include static magnets or electromagnets. The coupler may be contact or non-contact. The coupler may be oriented so that it engages with a drive member in an orientation-specific manner. For example, for magnetic couplers, the orientation of the magnetic poles on the coupler (and therefore on the friction gripper) may be arranged so that it mates with a drive member having a complimentary magnetic pole orientation. In some variations, the friction gripper (including or separate from the coupler) is keyed so that it only fits onto a drive member in a predetermined orientation.

The driver assembly typically includes the one or more drivers (e.g., motors) that move the drive members and therefore (through the couplers) the friction grippers in the proximal to distal line (axis). In some variations each drive member includes or is connected with a separate drive and capable of separately controlling the axial movement of that drive member, and therefore one of the friction grippers. In some variations the drive elements may share a drive element, but may still be separately moved, e.g., by controlling the engagement with the shared driver.

In any of the controllers described herein, the controller may be used within a sterile filed by enclosing it at least partially within a sterile barrier, such as a sterile bag, case, sleeve, etc. For example, a multi-part controller may be configured for use with a sterile barrier (e.g., sleeve) so that a first part (e.g., a cartridge including the friction grippers) may be sterile and used within the sterile field, while a second part (e.g., the reusable driver assembly) may be non-sterile but held within a sterile barrier (e.g., sleeve). The barrier may include a frame, cage, or other securement to hold the bag over the driver assembly so that the driver assembly may reliably engage with the cartridge and drive movement of the friction grippers through the sterile barrier.

For example, any of the controller systems described herein that are adapted to steer the distal tip of an elongate steerable device may include: a cartridge comprising two or more friction grippers arranged in a line extending proximally to distally, each friction gripper is configured to grip a portion of the elongate steerable device, further wherein each friction gripper is independently movable along the line extending proximally to distally; and a driver assembly comprising two or more drive members, wherein each drive member includes a drive motor connected to a magnetic coupler that is configured to magnetically engage one of the friction grippers when the cartridge is coupled with the drive assembly through a sterile barrier to drive movement of the one of the friction grippers in the line extending proximally to distally; wherein the cartridge and driver assembly are configured to be removably coupled together through the sterile barrier.

In some variations, the controller system includes a sterile barrier (which may be configured as a bag or sleeve) into which the driver assembly fits. The sterile barrier may include a cage, frame, or other securement within the sterile barrier into which the driver assembly fits.

As mentioned above, the friction grippers may each comprise a pair of gripping surfaces that may be clamped over the elongate steerable device. The friction grippers may each comprise a lock configured to releasably lock discrete portions of the elongate steerable device within the friction grippers.

The driver assembly and the cartridge may be held together (e.g., in some variations through the sterile barrier) by any appropriate attachment mechanism. Magnetic attachment between the cartridge and the driver assembly may be particularly useful, although other attachment (e.g., mechanical) mechanisms may also or alternatively be used. For example, an oriented magnetic attachment may be used between the cartridge and the driver assembly to both align and secure the cartridge to the driver assembly through the sterile barrier in a predetermined alignment. In general, the attachment between the cartridge and driver assembly may be orienting (e.g., keyed) so that the two are connectable only in a predetermined orientation.

Also described herein are elongate steerable devices for insertion into a subject's body, the devices comprising: an elongate body having a distal tip region, an intermediate region and a proximal handle region; a plurality of tendons attached to the distal tip region and extending proximally within the elongate body, wherein each tendon is coupled to a separate axially movable actuating region on an outer surface of the proximal handle region; and at least one divider in the distal tip region adapted to hold each of the plurality of tendons radially outward from a central core of the elongate body; wherein the at least one divider is adapted to prevent the tendons from tangling.

For example, a steerable device may be configured as a steerable guidewire device that may include: an elongate body having a distal tip region, an intermediate region and a proximal handle region; a plurality of tendons attached to the distal tip region and extending proximally within the elongate body, wherein each tendon is coupled to a separate axially movable actuating region on an outer surface of the proximal handle region; and at least one divider in the distal tip region adapted to hold each of the plurality of tendons radially outward from a central core of the elongate body; wherein the at least one divider is adapted to prevent each of the tendons from tangling.

As mentioned any of these devices may include a plurality of tendons (e.g., 2, 3, 4, 5, 6, 7, 8, etc.).

A divider may generally separate the tendons and apply force to keep them radially outward from the midline of the device. For example, a divider may comprise at least one core member within the distal tip region, though multiple core members (separate or connected) may be used. Core members may include separators having regions of alternating diameter extending along the length of the core member.

In general, any of the steerable devices described herein may be thin or narrow. For example, any of these devices may have an elongate body with a diameter of less than about 1 mm (e.g., less than 0.9 mm, less than 0.8 mm, less than 0.7 mm, less than 0.6 mm, less than 0.5 mm, etc.).

In some variations, the device may include multiple steerable regions. For example, an elongate steerable device for insertion into a subject's body, the device extending from a distal tip region to a proximal handle region in a proximal to distal direction, may include: a plurality of tendons, wherein each tendon of the plurality of tendons is attached to a distal bending region and extends from the distal bending region to the proximal handle region; a plurality of axial translation regions arranged along an outer surface of the proximal handle region, wherein each axial translation region of the plurality of axial translation regions is coupled to a tendon of the plurality of tendons; wherein the axial translation regions are elastically connected to each other, further wherein each axial translation region is configured to move in the distal to proximal direction to axially translate the tendon coupled to the axial translation region and thereby deflect the distal bending region to which it is attached.

In some variations an elongate steerable device for insertion into a subject's body includes: an elongate body having one or more distal bending regions, an intermediate region and a proximal handle region; a plurality of tendons, wherein each distal bending region is attached to one or more tendons, each of the tendons extending proximally within the elongate body, wherein each tendon is coupled to a separate axially movable actuating region on an outer surface of the proximal handle region; and at least one divider in a distal bending region, wherein the divider is adapted to hold each of the plurality of tendons radially outward from a central core of the elongate body; wherein the at least one divider is adapted to prevent the tendons from tangling.

BRIEF DESCRIPTION OF THE DRAWINGS

FIG. 1A shows an example of an apparatus (system) configured as an elongate steerable guidewire connected to a controller to drive steering of the distal tip (or other distal regions).

FIG. 1B shows an example of an apparatus (system) configured as an elongate steerable catheter connected to a controller to drive steering of the distal tip (or other distal regions).

FIG. 3A is another example of a side view of a distal end region of an elongate steerable device for insertion into a subject's body, configured as a steerable guidewire.

FIG. 3B shows a perspective view of the distal end region shown in FIG. 3A.

FIG. 3C shows a sectional view (taken though C-C' in FIG. 3A), looking distally, of the device shown in FIG. 3A.

FIG. 4A is another example of a side view of a distal end region of an elongate steerable device for insertion into a subject's body, configured as a steerable guidewire.

FIG. 4B shows a perspective view of the distal end region shown in FIG. 4A.

FIG. 4C shows a sectional view (taken though C-C' in FIG. 4A), looking distally, of the device shown in FIG. 4A.

FIG. 4D shows a perspective view of one variation of an inner core member, configured as a divider, which may be used with any of the apparatuses described herein.

FIG. 4E is a side view of the divider shown in FIG. 4D.

FIG. 4F shows an exploded view of the distal end region of the device shown in FIG. 4A.

FIG. 5A shows one variation of a proximal end region (e.g., the handle region, which may also be referred to as an actuator region or control region) of any of the apparatuses described herein, illustrating four axial translation regions; each axial translation region may be attached (e.g., within the coil) to a tendon wire that extends to a distal bending region. The proximal end region shown may be part of any of the device variations described, including those shown in FIGS. 1A, 1B, 2A, 3A and 4A.

FIG. 5B shows a slightly enlarged view of two elastically connected axial translation regions similar to those shown in FIG. 5A.

FIGS. 5C, 5D and 5E illustrate variations of axial translation regions that may be used. FIG. 5C shows an axial translation region formed from a portion of the coil forming the elongate body of the device, where the axial translation regions are formed by regions having a tighter pitch than the connecting regions. FIG. 5D shows an axial translation region formed by attaching a second material (e.g., cylinder) to a coli forming the elongate body of the device. FIG. 5E shows a separate region (e.g., cylindrical region) that is connected at either end to a coil such as the coil forming the elongate body of the device.

in FIG. 7 the partial view shows a pair of gripping surfaces and an axial translation region clamped between the gripping surfaces so that a driver (or drivers) can longitudinally (distally and proximally) drive translation both of gripping surfaces and therefore the axial translation region to actuate an attached tendon coupled to the axial translation region (not visible).

in FIG. 8 the partial view shows a pair of gripping surfaces and an axial translation region clamped between the gripping surfaces so that a driver can drive longitudinally (distally and proximally) translate one of the gripping surfaces and therefore the axial translation region to actuate an attached tendon coupled to the axial translation region (not visible).

in FIG. 9 the partial view shows a pair of rolling gripping surfaces and an axial translation region clamped between the rolling gripping surfaces so that a driver (or drivers) can drive translation of the gripping surfaces by driving rotation of the rolling surfaces and therefore displace the axial translation region to actuate an attached tendon coupled to the axial translation region (not visible).

in FIG. 10 the partial view shows a pair of gripping surfaces (one rolling and one longitudinally translating) and an axial translation region clamped between the gripping surfaces so that a driver (or drivers) can drive translation of the gripping surfaces and therefore displace the axial translation region to actuate an attached tendon coupled to the axial translation region (not visible).

FIGS. 15A-15E show detailed views of an example of an elongate steerable device (similar to the one shown in FIG. 14) for insertion into a subject's body, the device extending from a bendable distal tip region to a proximal handle region in a proximal to distal direction. FIG. 15A shows an overview of an entire length of this example of an elongate distally steerable device, while FIGS. 15B, 15C and 15D show greater detail of progressively more proximal regions from the distal end (shown in FIG. 15B) towards the handle region shown in FIG. 15E.

FIGS. 16A and 16B show greater detail of an assembly such as that shown in FIGS. 14 and 15A-15E, which may provide distal stiffness variations via an assembly of reinforced polymer tubes, each tube having a different flexural stiffness. In these figures, as in all of the figures shown unless the text specifically indicates otherwise, the dimensions shown are merely exemplary; these dimensions may be modified (increased/decreased).

FIG. 18A shows one example of a multi-part controller for actuating an elongate distally steerable device as described herein. In FIG. 18A, the multi-part controller includes a separate but connectable cartridge and a driver assembly, and in FIG. 18B the two have been connected to form the controller.

FIG. 24A is a top view of a protective bellows that may cover the inside of the driver assembly housing while allowing translation of the drive members. FIG. 24B is a top view of a driver assembly with the protective bellows removed.

DETAILED DESCRIPTION

Figure 2A:
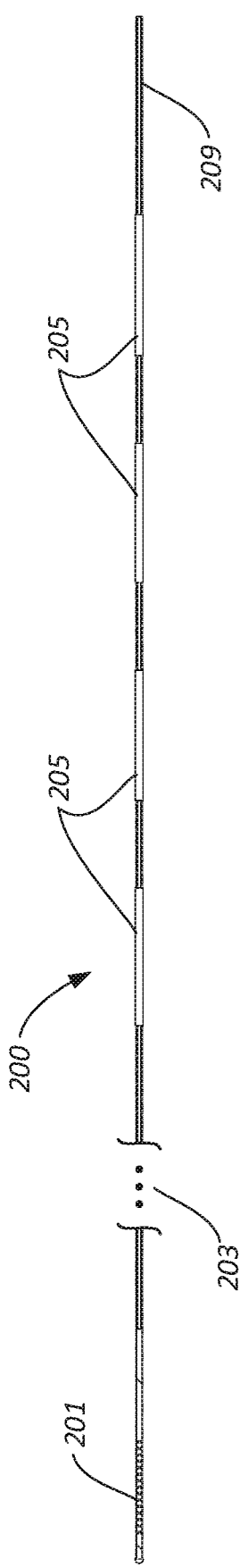
FIG. 2A is an example of an elongate steerable device for insertion into a subject's body, the device extending from a bendable distal tip region to a proximal handle region in a proximal to distal direction.

Elongate, steerable devices for insertion into a subject's body are described herein, including in particular very narrow (small diameter) devices that may be configured as steerable catheters and guidewires for use in interventional cardiology and neuroradiology, as well as methods of making and using them, controllers for controlling them, and systems including them. In general, these devices may have a bendable distal region (e.g., a distal tip region) and a proximal handle region, a plurality of tendons each attached to the distal bendable region and extending from the distal bendable region to the proximal handle region, and a plurality of axial translation regions in the proximal handle region. The axial translation regions may be arranged along an outer surface of the proximal handle region (or may form a part of the outer surface of the proximal handle region), and each axial translation region is coupled to a tendon for bending the bendable distal region. The axial translation regions may be elastically (e.g., extendably and compressibly) connected to each other, and configured to move in the distal to proximal direction to axially translate the tendon coupled to the axial translation region and thereby steer the distal bendable region.

The elongate steerable devices (e.g., guidewires, catheters, etc.) described herein may generally be any appropriate length, such as, e.g., between about 0.5 m to about 3.5 m. For example, an elongate, thin and steerable catheter configured as described herein may be between about 1 m and 1.5 m long. An elongate, thin and steerable guidewire may be, for example, between about 1.7 m and 2.5 m long (e.g., approximately 1.9 m long).

As used herein, a subject may refer to any subject, human or animal. A subject may also be referred to as a patient. As used herein, a tendon generally includes a flexible and relatively inelastic elongate length of material, such as a wire, cord, line, etc. For example, a tendon may be a tension wire. In some examples the tendon has a sufficient column strength to allow pushing as well as pulling of the tendon to actuate movement of a device. As used herein, "adjacent" may refer to components (e.g., tendons) that are next to each other, including extending in parallel with each other. Adjacent elements may, but do not have to be, contacting each other. For example, adjacent tendons do not need to be in contact, although in some variations they may be (and may be referred to as immediately adjacent), but may be separated by other elements. Similarly, adjacent axial translation regions may be nearest neighbors to each other (compared to other axial translation regions) but need not be contacting each other.

As used herein, an elongate object may refer to an object or component that is longer than it is wide (and/or high). In particular, the elongate objects, including the elongate steerable devices described herein, may include an elongate body that is much longer in a distal to proximal axis than in transverse cross-section. For example, the steerable guidewires and steerable catheters described herein include an elongate body that extends in the long (proximal to distal) axis.

As used herein, the phrase "elastically connected" means that the elements being elastically connected are connected so that the region between the elements may be extended (e.g., stretched) or collapsed (e.g., compressed) to change the relative distance separating the elements that are elastically connected. In some, but not all, variations the elastically connected regions may be biased so that a restoring force tends to restore the relative distance separating the two elements that are elastically connected. In some examples the elastically connected elements are connected so that the distance between the elements may be made shorter or longer without a substantial restoring force tending to restore a predetermined separation between the two elements. Regardless of the bias or restoring force, the spacing between elastically connected elements may be adjusted to extend or compress the distance between the two elements and their original separation distance (e.g., a predetermined separation distance) may be manually or automatically restored.

FIGS. 1A and 1B illustrate variations of elongate, steerable devices for insertion into a subject's body. In FIG. 1A the device 100 is configured as a steerable, extremely low-profile guidewire that may be suitable for use in interventional cardiology and/or neuroradiology procedures. The distal end of the device (distal tip region 102) is bendable, as shown by the dashed line, and includes a plurality of internal tendons (not visible in FIG. 1A). The device extends distally to proximally through an intermediate region to a proximal handle region 105 that is shown connected to a controller 107. The device may be formed of a coil (e.g., helical coil).

The proximal region may include a plurality of axial translation regions (e.g., "sliders") formed into/onto the elongate body at the proximal end. For example, the axial translation regions may be formed by regions of the coil that have a different pitch, as illustrated in FIGS. 5A-5E, below. The axial translation regions may be formed by welding hypotubes to the coil, or by inserting hypotubes between coil regions.

Any of the elongate, steerable devices described herein could have a coating (e.g., a hydrophilic coating). In some variations a portion of the elongate body (e.g., the intermediate region) may be a hypotube (e.g., a flexible hypotube). Alternatively, the entire device could be made of one coil (e.g., a spring), which may or may not include an outer (e.g., polymeric) coating.

The distal steerable region may be both small diameter (e.g., less than 1 mm, less than 0.9 mm, less than 0.8 mm, less than 0.7 mm, less than 0.6 mm, less than 0.5 mm, etc.), and may be both soft and flexible, so that it can be bent. Further, the tendon attachment sites can be separated from each other and the tendons may be held close to the outer wall of the elongate body (spaced out) along the entire bending length, so that the tendons are each as far from the center line as possible.

FIG. 1B illustrates another variation of an elongate, steerable device for insertion into a subject's body. In FIG. 1B, the apparatus 120 is configured as a catheter. The distal tip region 122 is bendable, and the proximal end 125 includes a plurality of axial translation regions that are shown within a controller 107. A guidewire 127 is shown passing through the catheter.

FIG. 2A shows another variation of an elongate, steerable device for insertion into a subject's body, configured as a thin steerable guidewire 200. In this example, the distal tip region is a steerable distal tip 201. An intermediate body region 203 has been shortened (e.g., to show only a few mm of length; in practice the actual length may be 1 m or more). The proximal end includes sliding elements (a plurality of axial translation regions 205) and an end stop 209.

Figure 2B:
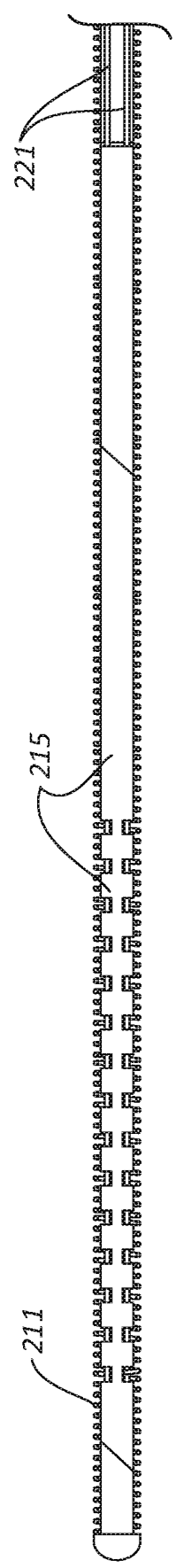
FIG. 2B shows an enlarged sectional view of the distal end (tip) region of the device of FIG. 2A.

The steerable tip in FIG. 2A can be selectively bent by tensioning one or more of the tension wires 221. The body of the guidewire includes a hollow lumen to house the tension wires, as shown in FIG. 2B. At the proximal end, each tension wire is fixed to a separate axial translation region (sliding element 205), which is used to control the tension in the wires.

As mentioned above, a tension wire (e.g., a tendon) may be a wire, e.g., pull wire/push wire, rod (e.g., pull rod/push rod), strand, fiber, etc., or the like. The tendons may be attached to the distal bending (e.g., tip) region at radially offset attachment sites. In particular, the tendons ("tension wires") may be multi-filament (e.g. yarn or braid) tension wires. Tendons may also be monofilaments (e.g. steel or Nitinol wire). In some variations, multi-filament tendons may interplay (e.g., pulling one often pulls them all) less than monofilaments inside the guidewire, and therefore may be preferable. For example, a multi-filament tendon may comprise a yarn with an OD of approximately 0.04 mm, comprising, e.g., five individual fibers each measuring about 0.01 mm.

Figure 2C:
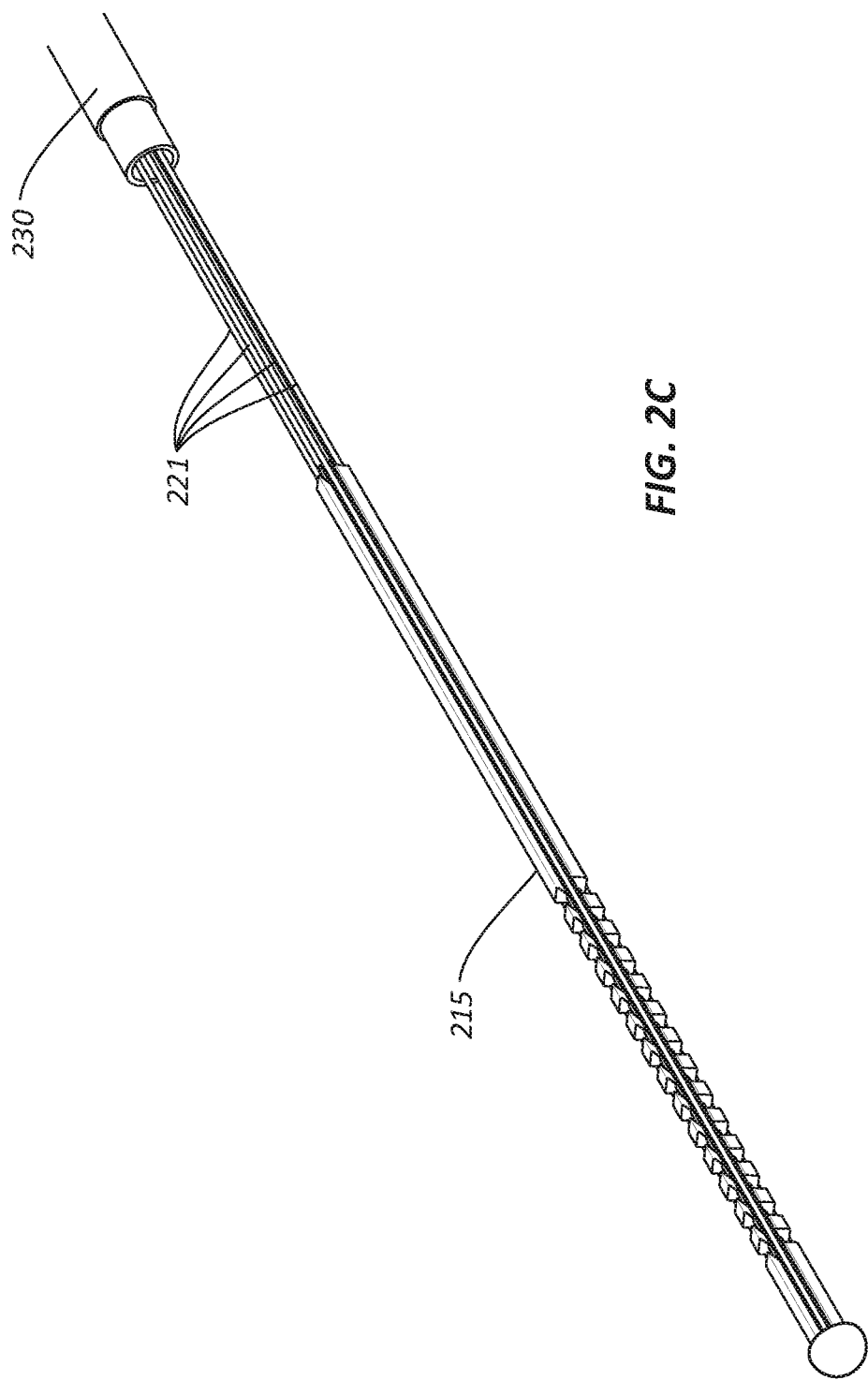
FIG. 2C shows an enlarged perspective view of the distal (tip) region of the device of FIG. 2A without the distal spring.

FIG. 2B shows a cross-sectional, 2D close-up of the distal end of the device of FIG. 2A. FIG. 2C shows an isometric close-up of the same distal end with the distal spring (coil 211) hidden. In this example, the distal tip has a bendable core 215, four tension wires 221 (only two visible in FIG. 2B) and a flexible encasing coil or spring 211. The tension wires 221 are fixed to the very distal tip of the core, as is the spring. The core may either be a single piece or a multi-part core, and may either be made of a relatively flexible (e.g. a polymer) or a relatively rigid (e.g. a metal) material, or a combination of the two. The core 215 may act as a spacer or placeholder for the tension wires, to ensure that the forces imparted to the core, and more generally on the distal tip, by the tension wires act in the correct directions to produce bending of the tip. Without the core (i.e. just with the spring or a hollow flexible section], testing shows that the bending is unpredictable and inefficient. In addition, the core may also prevent twisting of the tension wires, both within the distal tip and along the body 230 of the guidewire, which may cause the wires to bind up and prevent the tip from deflecting. In some examples the device includes a single piece, soft, polymeric core. Optionally, the core may be secured at both ends to make the tip deflection more efficient.

FIGS. 3A-3C illustrate another variation of a bendable distal tip region of a device configured as a steerable guidewire. FIGS. 3A and 3B show a distal segment of a steerable guidewire that does not have a core. In this example, the distal spring is manufactured with dividers or spacers 301, 303, 305, 307 (4 dividers are shown), which locate the tension wires 322, 324, 326, 328 in their relevant quadrants and prevent them from moving to the center line of the guidewire. As shown the spacers are formed by transverse lengths of the spring/coil material forming the body of the distal region. The tendon wires 322, 324, 326, 328 pass through the openings in the crossed spacers. This is apparent from the distal-facing view shown in FIG. 3C taken though section C-C' in FIG. 3A.

FIGS. 4A-4F illustrate another variation of a bendable distal tip region of a device configured as a steerable device. The device may (like a steerable catheter) include a central lumen. This device includes a multi-part core. It is similar to the single-part "spinal" core shown in FIG. 2B, but includes multiple pieces forming the core. This design may have an increased flexibility for bending. An outer spring (coil) 403 wraps over the inner core and four tendons 422, 424, 426, 428. The core holds the tendons in a radially outward position, as apparent in the distal-facing sectional view is shown in FIG. 4C (taken through section C-C' of FIG. 4A). The tendons connect at the distal end to a cap 433.

An exploded view of the distal end is shown in FIG. 4F, including the outer coil region 403, tendons 422, 424, 426, 428, cap 433, and core 415. The core is formed of a plurality of individual core elements 417. FIG. 4D shows an individual core element in perspective and end views, respectively.

Figure 4H:
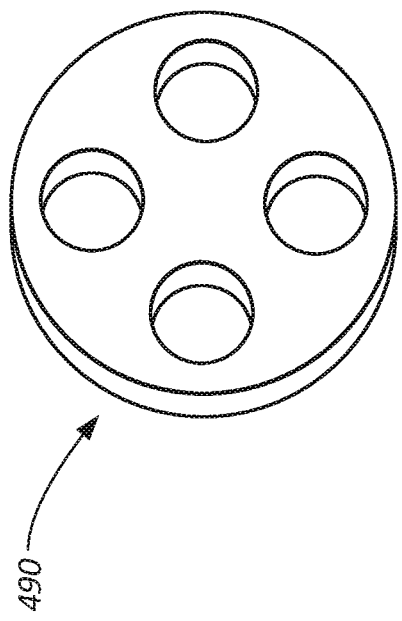
FIGS. 4G and 4H show side perspective and end perspective views, respectively, of another variation of a core (inner core) member configured as a multi-lumen member, having a channel or lumen for each of the tendons
Figure 4G:
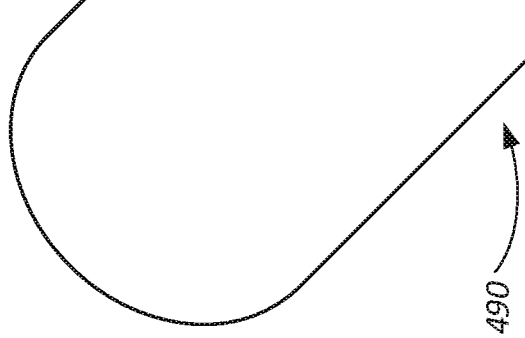

FIGS. 4G and 4H illustrate another variation of a core element that may be used. In this example, the core is a multi-lumen extrusion (MLE) core that may be helpful in separating the tension wires, e.g., at the distal end region. In this example, the multi-lumen extrusion core includes four transverse lumens, each of which may hold a tendon, and separate the tendons from each other. In one example, the OD of this core is approx. 0.24 mm (e.g., between about 0.1 mm and about 0.5 mm), and diameter of each of the four lumens is approx. 0.065 mm (e.g., between about 0.050 mm and 0.09 mm). In an elongate steerable device including a multi-lumen extrusion 490 such as the one shown in FIGS. 4G-4H, each of the lumens 499 may have a single tension wire running through it. Once the tension wires are assembled in place they are retained in the lumen. The apparatus may therefore include a multi-lumen extrusion core that is about 30 mm long (e.g., between 20 mm and 50 mm, between 20 mm and 40 mm, between 25 mm and 35 mm, etc.) and located at a very distal end of the apparatus.

In general, the distal segment, whether it includes a core or not, is configured to be flexible so as to permit maximum bending, and to correctly orient the tension wire forces and prevent the wires from tangling, so that the bending amplitude and direction are predictable and repeatable.

In any of the apparatuses described herein (which may include systems and/or devices), a portion of the apparatus, e.g., the elongate steerable devices described herein, may be radiopaque. For example, a distal tip region may be radiopaque. In some variations, particularly use for interventional cardiology but not limited to this use, the apparatus may include a distal tip region of approximately 30 mm of the guidewire that is radiopaque. In standard wires, this may typically be achieved using a platinum or tungsten based coil (e.g., either a pure metal or an alloy). In some variations, the apparatus includes a radiopaque region formed using a tungsten coil. Alternatively platinum based materials may be used (although it may be preferable to use less malleable materials, so that the elongate steerable device has a lower hysteresis, e.g., failing to spring back and "zero" the guidewire when the tension wires are de-tensioned).

FIGS. 5A-5E illustrate variations of a proximal region including a plurality of axial translation regions arranged along an outer surface of the proximal handle region. Each axial translation region of the plurality of axial translation regions is coupled to a tendon of the plurality of tendons. In FIG. 5A, a portion of the proximal region includes four axial translation regions ("sliders") 503, 505, 507, 509 that are elastically coupled to each other (to adjacent axial translation regions) by coil/spring regions 511, 513, 515. FIG. 5B shows a cross-sectional 2D close-up view of the proximal end of one example of an apparatus. In FIG. 5B, each sliding element is fixed to springs at each end to allow the element to slide distally or proximally in the long axis of the device by compressing/extending the spring regions between the axial translation regions. The axial translation regions may be actuated via the application of an external force. For example, the axial translation regions may be moved (actuated) by hand, e.g. using fingers or tweezers, by attachment to a controller, e.g., having some device grip the elements and move them, by electromagnetics, e.g., making the sliding elements out of magnetic materials and placing electromagnetic coils around them, and by electrostatics, e.g., charging the sliding elements and repelling/attracting them to adjacent elements that move.

Thus, in any of the devices described herein the outer diameter of the device (guidewire, catheter, etc.) may be maintained as constant, so that another device (e.g., a catheter) can be passed over the top. In the example shown in FIGS. 2A, 2B, 2C and 5B, the entire device from the proximal end to the distal end has an outer diameter of less than or equal to about 0.36 mm.

FIGS. 5C, 5D and 5E illustrate variations of axial translation regions that may be used. In FIG. 5C, the axial translation region is a coil region having a tighter pitch than the compressible/expandable regions adjacent to the axial translation region. In some variations the coils forming the axial translation region may be fused, glued, or otherwise connected together. For example, in FIG. 5D an additional hypotube member 514 is shown attached to form the axial translation region. Alternatively, in FIG. 5E the axial translation region is formed of a separate hypotube that is coupled at either end to coil regions. A stationary core may extend through the proximal handle region to form a guide rail for the axial translation regions to slide on (not shown), and the axial translation regions may be elastically connected to adjacent axial translation regions or to the stationary guide rail core.

Figure 14:
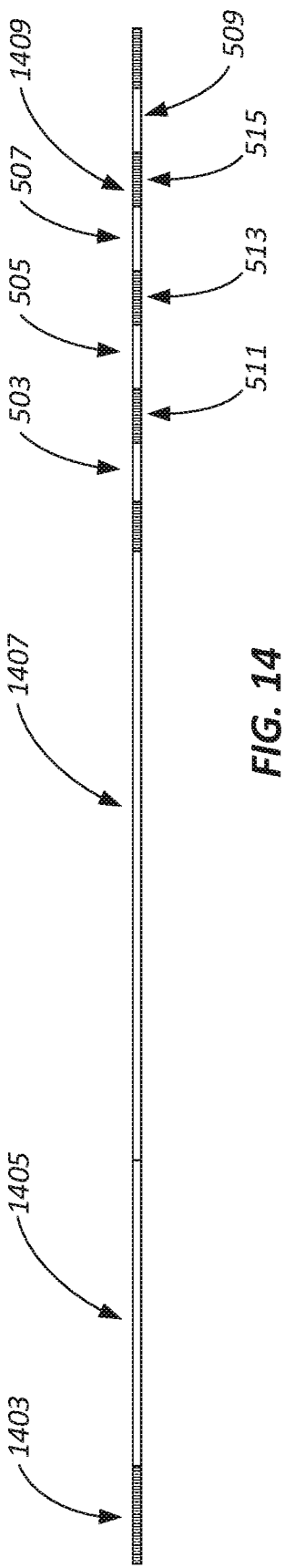
FIG. 14 shows another example of an elongate steerable device for insertion into a subject's body, the device extending from a bendable distal tip region to a proximal handle region in a proximal to distal direction.

Another example of an elongate steerable device for insertion into a subject's body is shown in FIG. 14. In FIG. 14, exemplary dimensions are provided for illustration only; these dimensions are not intended to be limiting, and alternative dimensions (or ranges of dimensions) may be used. For example, FIG. 14 shows an example of an elongate steerable device configured as a reinforced polymer tubing guidewire; the device is shown having a length of about 1900 mm, which may be broken out into a distal tip region ("distal coil") 1403 of length 30 mm, a reinforced polymer tubing assembly region 1405 ("variable stiffness region") of approximately 390 mm, a body region 1407 ("hypotube body") of length 1330 mm, and a proximal handle region 1409 ("proximal coil") of about 150 mm. Note that the device shown is not to scale, as reflected by these approximate lengths. In FIG. 14, the distal tip 1403 may be radiopaque, as described above, e.g., by including tungsten. The variable stiffness region in this example is formed of a reinforced polymer tubing assembly that is configured, as will be described in greater detail below, so that the stiffness varies from the proximal end (e.g., the handle end) which is relatively stiff, as is the hypotube body 1407, to the more flexible distal end. This gradual change in stiffness may prevent buckling of the device. The body region 1407 in this example is formed of a hypotube that may be laser cut to modify its stiffness (e.g., laser cut stainless steel), an example of which is shown in FIG. 17D, below. The proximal end may be formed as a proximal handle (as described and discussed above, including axial translation regions ("sliders") 505, 507 that may be coupled to the tendons and separated from each other by intermediate coil/spring regions 513 that allow the distance between the sliders to be adjusted.

As mentioned, in FIG. 14 the device includes a body that is formed of a stainless steel hypotube. In some variations (described above) the body may be formed of variable pitch/pre-tension springs. In FIG. 14, the body is formed of a relatively stiff hypotube, e.g., 28 gauge, thin-wall ("304V") stainless steel. As illustrated and described below for FIG. 17D, the device may be configured to include a smooth transition between the relatively stiff hypotube and the very flexible, atraumatic distal coil by selectively laser cutting the hypotube towards its distal end. A laser cut helix may be included, running along a distal region (e.g., the distal 400 mm) of the hypotube, with a pitch that varies (e.g., from approx. 5 mm proximally to approx. 0.1 mm distally). The laser cut hypotube may then join onto the distal coil. The laser-cut region at the end of the hypotube may be any appropriate length (e.g., 200 mm, 300 mm, 400 mm, 500 mm, etc.).

Alternatively or additionally, the distal stiffness transition from the stiff hypotube to a flexible distal coil may be formed by assembling a coil or braid-reinforced polymer tube in between the body and the distal tip region. As an example of this configuration, FIGS. 15A-15E illustrate an elongate steerable device designed using this configuration. In FIG. 15A, the overall (not to scale) regions of one variation of an elongate steerable device (e.g., configured as a steerable guidewire, catheter, etc.) are shown, including a flexible distal tip region 15B (shown in greater resolution in FIG. 15B), as well as a reinforced tubing sub-assembly (FIGS. 15C and 15D), a body region 1505, and a proximal handle region 15E (shown in greater detail in FIG. 15E).

As shown, the distal coil region 1504 may be connected to a varying stiffness region (reinforced tubing sub-assembly 15C) by a sleeve 1507. This varying stiffness region may be formed of a combination of different regions, such as coils having different stiffnesses (durometers), such as a 55D coil, 72D coil, 63D coil, 72D braids, and the like. The coils may be overlapping and/or may be connected by sleeves.

Another, similar variation is shown in FIGS. 16A-16B, showing just the varying stiffness region formed as a reinforced tube. In this example, the distal coil is not shown, nor is the body region. The PI/braid/72D tube 1604 is stiff (but slightly less stiff than the hypotube body region, not shown), the PI/coil/63D tube 1606 is less stiff, the 72D/coil/72D tube 1608 is less stiff again, and the 63D/coil/40D tube 1610 is even less stiff (but slightly stiffer than the distal coil, not shown). In this example, exemplary dimensions are shown (in mm). For example, a 55D coil 1610 may have dimensions (in inches) of a 0.0098"×0.0138" tube with 0.0005"× 0.0025" coil @ 150 WPI; a 72D coil may be a 0.0098"× 0.0138" tube with 0.0005"×0.0025" coil @ 150 WPI; a PET shrink tube (e.g., heat shrink tubing) may have a 0.0002" wall thickness; a 72D PI-braid region 1604 may be a 0.0098"×0.0138" tube with 0.0005"×0.0025" braid @ 70 PIC half load; a 63D PI-coil may be a 0.0098"×0.0138" tube with 0.0005"×0.0025" coil @ 150 WPI; and a PI-sleeve may be a 0.0079"×0.0089" tube.

In some variations the devices described herein may be formed using polyimide (PI) sleeves and PET heat shrink to make the device easier to assemble. Generally PI sleeves may be placed inside the inner lumen to add extra support, and PET heat shrink may be placed on the outer surfaces to seal the inner lumen and prevent blood from penetrating or to ensure that the OD is smooth and dag-free for passing other devices over the top.

FIGS. 17A-17D illustrate another variation of an elongate steerable device having a flexible distal end (tip) that is steerable using the sliding controls on the proximal handle coupled to very thin tendons, as described above (dimensions shown for length are exemplary only and are in mm). In FIGS. 17A-17D, the varying flexibility (stiffness) approaching the distal end of the device is achieved by cutting (e.g., laser cutting) the hypotube forming the body. For example, the body of the device, a distal portion of which is shown in greater detail in FIG. 17D, is formed of a laser cut hypotube in which the stainless steel tube is helically cut to different pitches (narrower pitching being generally more flexible, less stiff than less narrow pitch cuts) towards the distal end where it may be laser welded or otherwise attached to the distal tip, formed by a coil. The tip region is shown in greater detail in FIG. 17C.

Figure 17A:
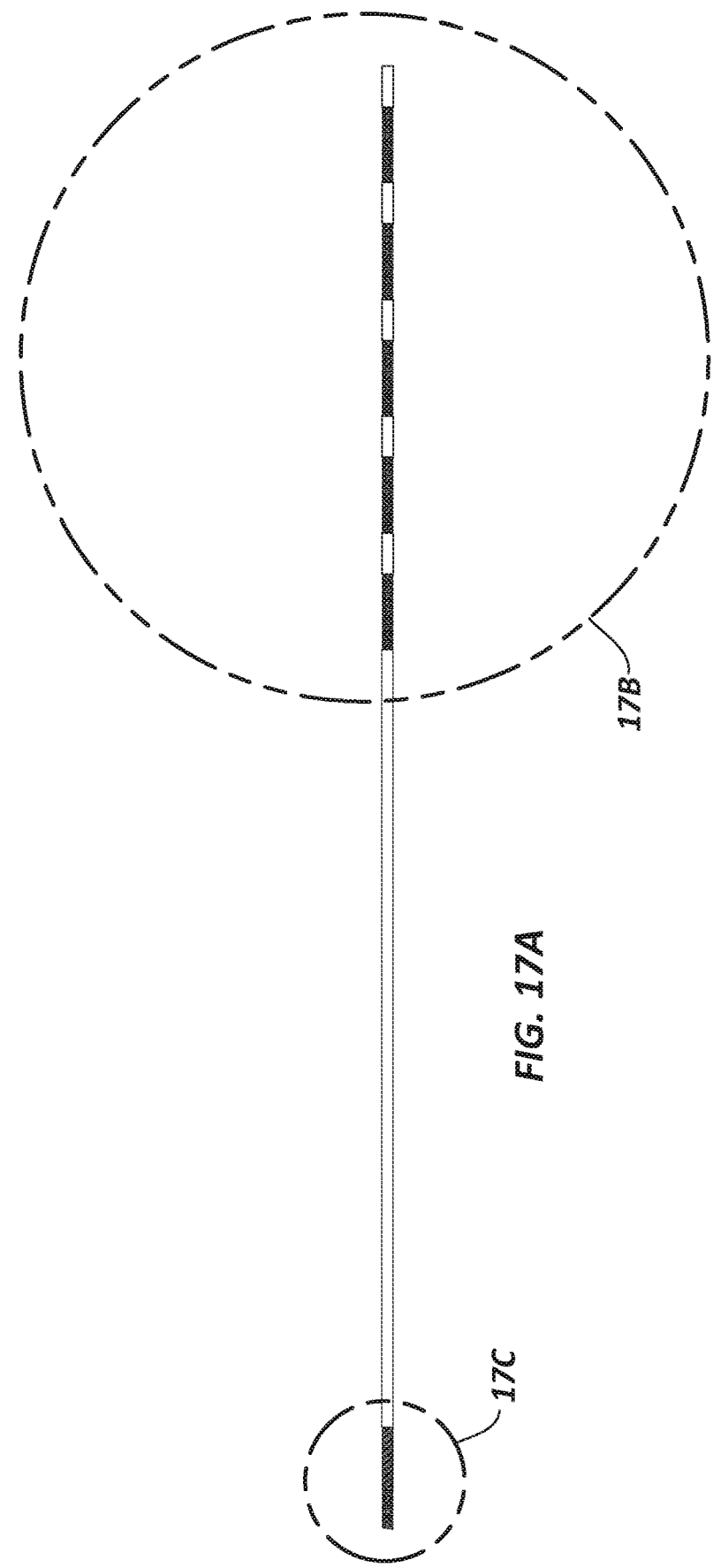
FIG. 17A shows another example of an elongate distally steerable device.
Figure 17B:
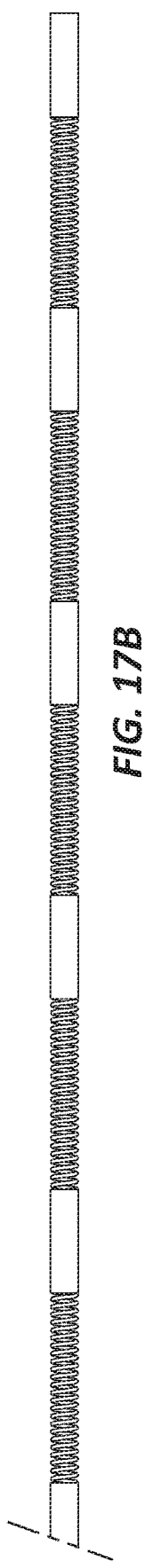
FIG. 17B shows an enlarged view of the handle region at the proximal end of the device of FIG. 17A, including multiple sliding elements (axially translating control elements) that may be used to actuate individual tendons to steer the tip of the device, as descried herein.
Figure 17C:
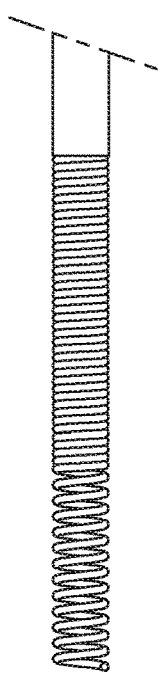
FIG. 17C shows an enlarged view of a portion of the distal tip region.
Figure 17D:
FIG. 17D shows a portion of the body region between the proximal handle and distal tip, illustrating a laser-cut hypotube.

The proximal handle region for controlling steering, shown in greater detail in FIG. 17B, in this example is a stainless steel coil having regions of different pitch. Some of these regions correspond to the sliding elements (sliders) described above for coupling to and actuating the tendons to steer the tip of the device.

Controller

Figure 6:
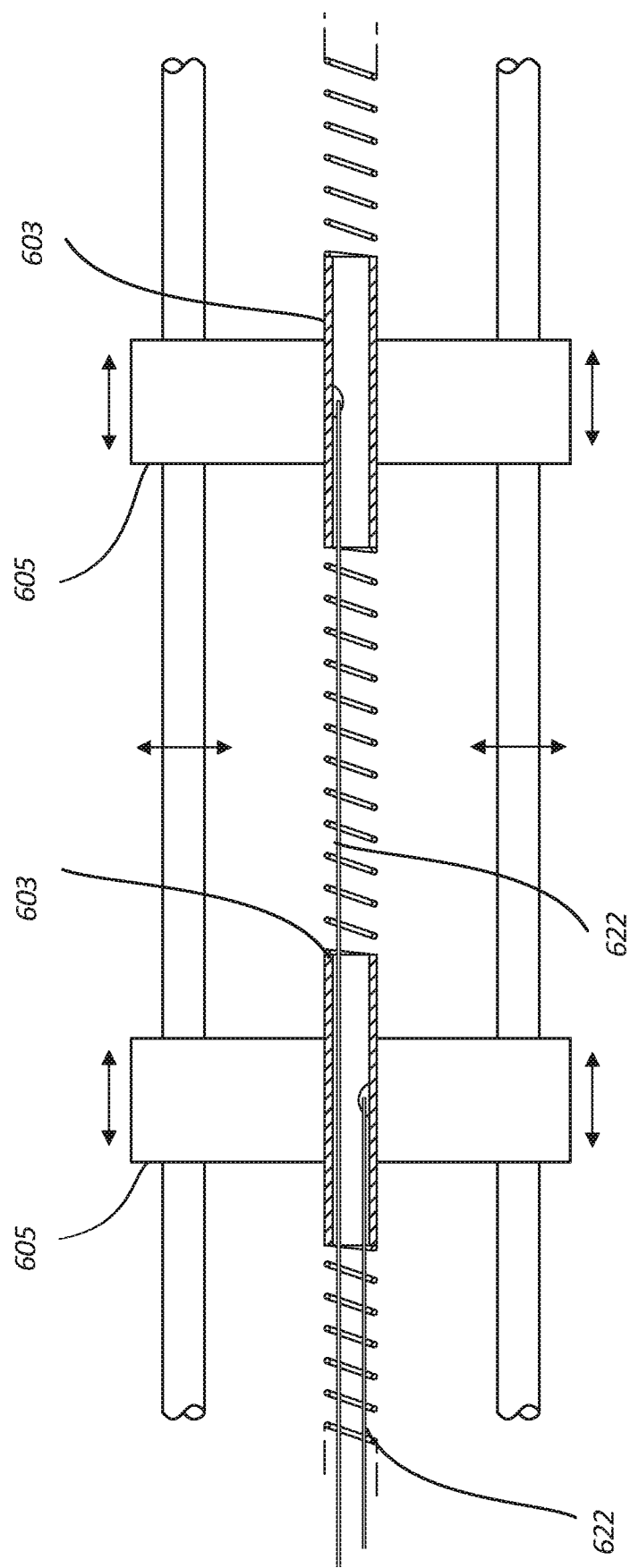
FIG. 6 schematically illustrates a portion of a controller coupled to a proximal handle region of an elongate steerable device.

Also described herein are apparatuses (e.g., devices, systems, etc.) for controlling actuating of the linearly-arranged sliding elements that actuate the steering of the distal tip. For example, a system including the devices described above may include a controller for steering the devices. In general, a controller may be referred to as a controller, actuator, steering control, or the like. For example, returning now to FIG. 6, this figure shows schematics of one variation of a friction-based actuation system (controller). For four axial translation regions 603 (two such sliding elements are shown), four sets of grippers 605 (which may be referred to herein as friction grippers or simply grippers) may be used to grab the axial translation regions 603 and selectively and independently slide them distally or proximally. Each of the axial translation regions may be coupled to a tendon wire 622. The grippers 605 may all be housed in a gripper assembly (or control unit). The control unit can be connected to and disconnected from the guidewire at will. As such, when a clinician wishes to steer and navigate, she/he may connect or have the controller connected to the device. Then, if the clinician wants to pass a catheter or other delivery device over the guidewire, he/she may disconnect the control unit. In the controller, the grippers 605 may be actuated by independent motors that are housed within the control unit, or by a single motor that drives each of the grippers (e.g., pairs of grippers). These motors may be, for example, electromagnetic servos, or may be piezoelectric motors. The use of motors (rather than manual actuation by hand) may be advantageous because, firstly, the proximal tension wire displacement required to bend the distal tip by 90 degrees is only a few millimeters. Achieving such resolution by hand for precision navigation may be challenging. Secondly, the motors described herein may be programmed to hold a commanded position via closed-loop feedback. In one exemplary system, the clinician controls these motors and the steering of the guidewire/catheter via a user-friendly joystick interface.

In any of the exemplary devices, the connecting regions between axial translation regions do not have to be springs. In the example shown in FIG. 5E, the intermediate spring regions are laser welded onto 350 μm OD tubes (250 ID); the axial translation region has a length (e.g., approximately 5 mm, 7 mm, 8 mm, 9 mm, 10 mm, 11 mm, 12 mm, etc.) long; the intervening springs may be a predefined length at rest (e.g., 3 mm, 4 mm, 5 mm, 10 mm, 12 mm, 15 mm, 20 mm, 25 mm, etc.) long.

In any of the variations, a guide mechanism may be included as part of the device to keep the sliders concentric with center line of the device. For example, the springs may be connected to each other, or can have a guide wire (or other core structure) through the middle of the device (e.g., similar to a core wire at the distal end) and have sliders running on this guide/core wire.

Figure 7:
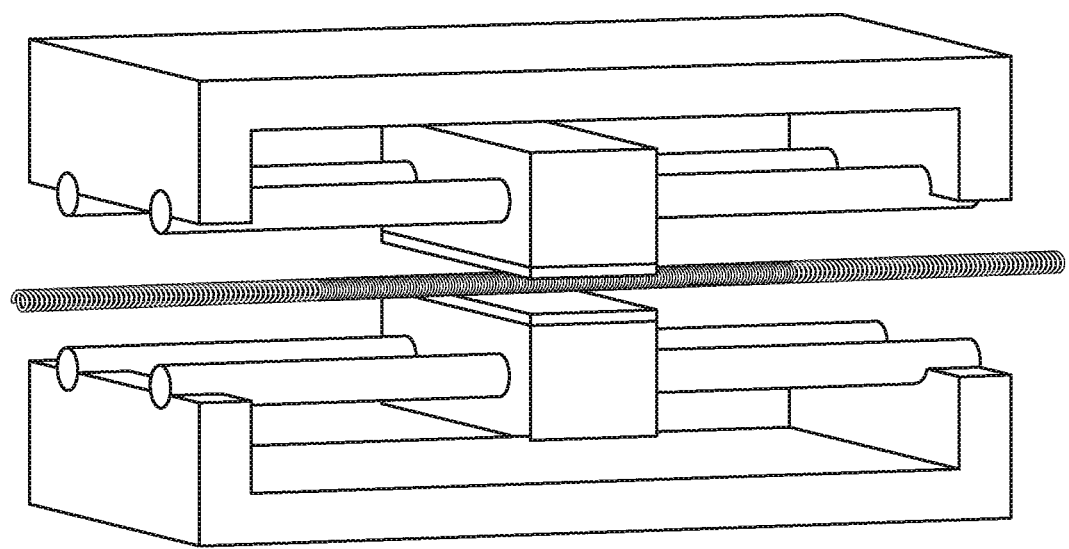
FIG. 7 shows a partial perspective view of one variation of a controller for actuating a steerable device such as those shown in FIGS. 1A-5F.

FIGS. 7-11B illustrate alternative variations of grippers that may be used with any of the controllers described herein. For example in FIG. 7, a pair of opposing grippers may be used to clamp over and control an axial translation region, as shown. One or both members of the pair of grippers may be moved axially to actuate bending/unbending by a corresponding tendon that is attached to the axial translation region shown. FIG. 7 shows two friction grippers forming a pair that run on smooth rails. The elements connecting the grippers to the rails may preferably made from a low friction material (e.g. PTFE) to minimize the friction with the rails (which are preferably mirror-polished stainless steel or similar). Each sliding element (gripper) may include a grip pad or surface that contacts the axial translation region of the device. The grip pads may preferably be made of a high friction material (e.g. silicone rubber) to maximize the friction with the guidewire.

Figure 8:
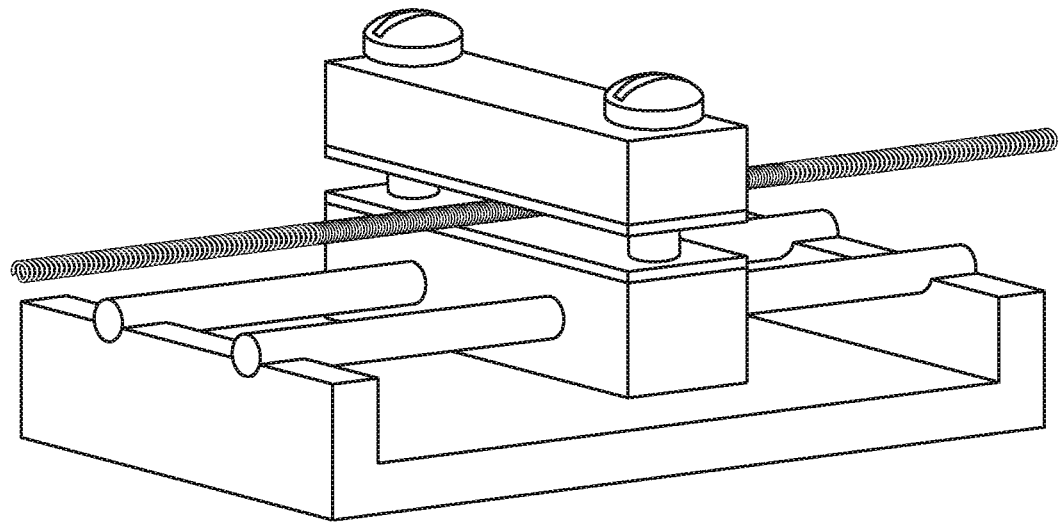
FIG. 8 shows a partial perspective view of another variation of a controller for actuating a steerable device such as those shown in FIGS. 1A-5F.

In FIG. 8, the gripper region is similar to that shown in FIG. 7, but only one side of the gripper is connected directly to the actuator (e.g., motor). Thus, FIG. 8 includes only one sliding element and one set of rails. The frictional gripping force on the guidewire may be generated by clamping it between two parts (or between a single part in some variations). The first part is the sliding element (gripper), and the second is an upper jaw. In FIG. 8, the clamping force is generated by two screws. The clamping force could be generated with one screw, or via an entirely different method using no screws at all.

Figure 9:
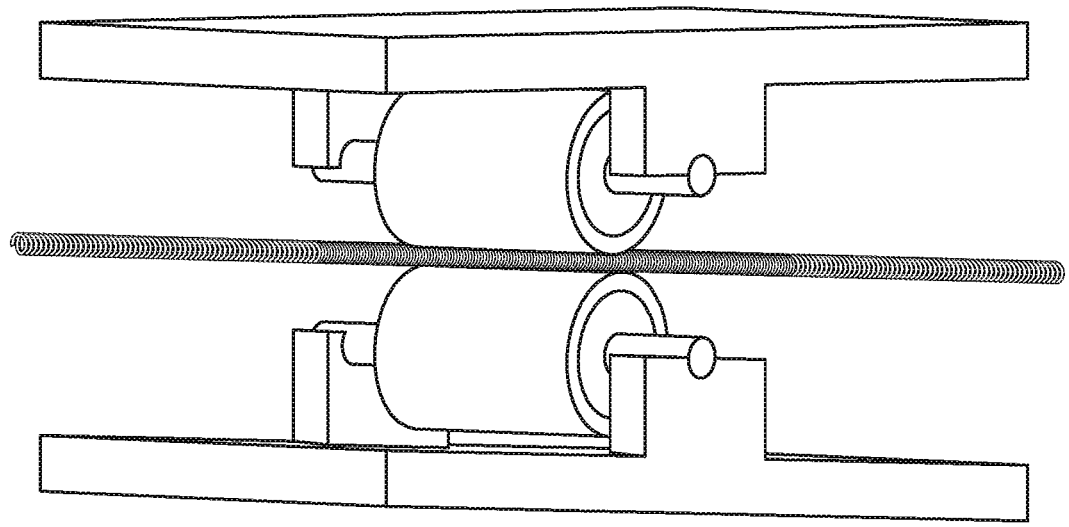
FIG. 9 shows a partial perspective view of another variation of a controller for actuating a steerable device such as those shown in FIGS. 1A-5F.
Figure 10:
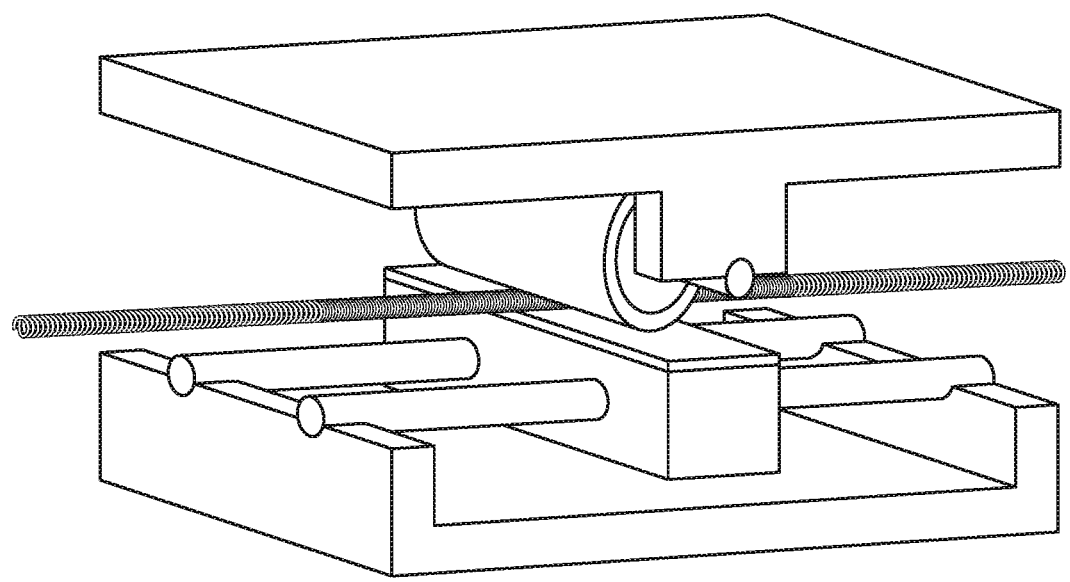
FIG. 10 shows a partial perspective view of another variation of a controller for actuating a steerable device such as those shown in FIGS. 1A-5F.

FIG. 9 shows a pair of clamping grippers that are configured as rollers; actuation of the roller may drive the axial translation region within the gripper pair either distally or proximally. Similarly, FIG. 10 shows a hybrid gripper pair having both a roller and a longitudinally translating gripper. FIG. 10 shows a sliding element (frictional gripper) that has been replaced by a rolling element. The rolling element may include a grip pad (or more accurately a grip tire). The rolling element can be made of a low friction material such as PTFE and run directly on a polished shaft, or it can contain bearings. For example, the rolling element can be a single radial ball or roller bearing, with a grip tire fitted to it. Alternatively, it can be an elongate hollow cylinder with a small bearing fitted into each of its ends. A further alternative is to press-fit the rolling element onto the shaft, and support the shaft at its ends on bearings (e.g. using pillow blocks). In this case, the rolling element can be made of any material.

Figure 11A:
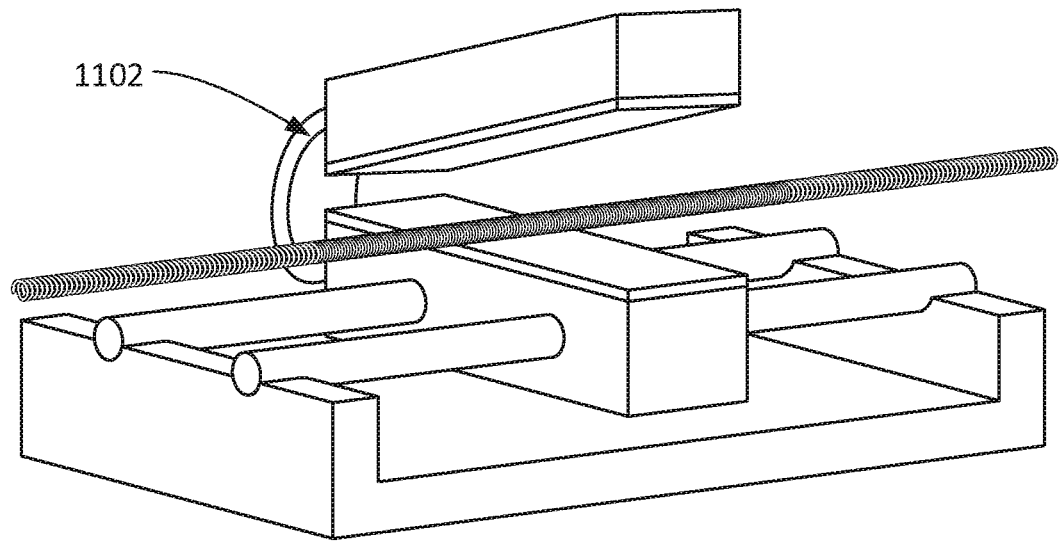
FIG. 11A shows a partial perspective view of another variation of a controller for actuating a steerable device such as those shown in FIGS. 1A-5F.
Figure 11B:
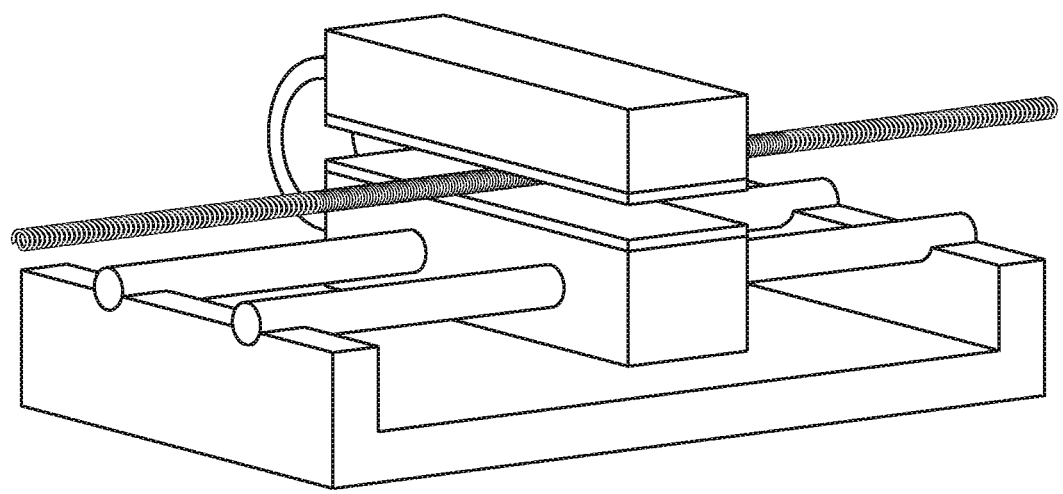
in FIG. 11B, the pair of gripping surfaces of the device are shown clamped onto the axial translation region and a driver (e.g. motor) can drive translation of the gripper surfaces distally or proximally (longitudinally) to actuate an attached tendon coupled to the axial translation region (not visible).

FIGS. 11A and 11B illustrate a controller having a hinged region 1102 that connects the upper and lower grippers and allows the controller to shut over the proximal end of the device so that it can be actuated. In FIG. 11A, the controller is open, and the axial translation region of the device is placed between the upper and lower gripper regions. FIG. 11B shows the controller clamped over the axial translation region. FIGS. 7-11B show partial views of controllers, illustrating only a single pair of grippers; as mentioned, a controller apparatus may include a plurality of independently operable grippers that can actuate a plurality of axial translation regions.

In FIGS. 11A and 11B, the hinge could have a spring connected to either provide a normally-open or normally-closed configuration. The user would then apply force to move the hinge to the non-normal position. Once in the non-normal position, a latch or clip (not shown) could hold the hinge in place until the latch or clip is removed. Alternatively, no spring may be used at all, and the clamping pressure may be provided by the user or other means. For example, a user could squeeze the hinge shut and a latch or clip could hold it in place until the user disengages this latch or clip.

In variations having pairs of frictional grippers, both of the sliding elements and/or rolling elements may be actuated, or one may be actuated and the other simply follows (as a counter-support) due to a transfer of the actuation force via friction through the guidewire segment. As mentioned, any of these sliding/rolling elements can be actuated by hand, via mechanical mechanisms (e.g. dials, pulleys, levers, gears) or via electromechanical means (e.g. actuators or motors). For example, small and precise actuators/motors may be used, as they provide the displacement resolution and precise force control. Any of the actuators/motors may be used in a closed-loop configuration (e.g. servos), as this may provide electronic position feedback for monitoring safety and automatic positional zeroing. Actuation forces via any means (hand, mechanical or electromechanical) can be applied to the sliding/rolling elements directly or through one or more intermediary elements. Examples of intermediary elements include ropes, pulleys, gears, lead screws, shafts, bearings and the like.

Figure 12A:
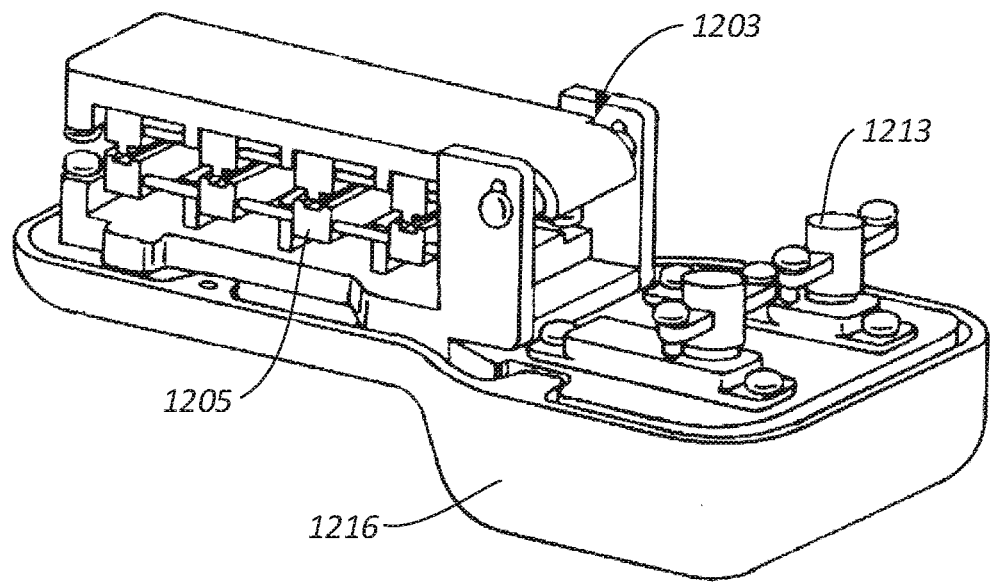
FIG. 12A illustrates a side perspective view of one variation of a controller having a plurality of clamping pairs of gripper surfaces, each securing to an axial translation region and each independently movable to actuate different tendons and steer a distal region (e.g., the distal tip) of a steerable device.
Figure 12B:
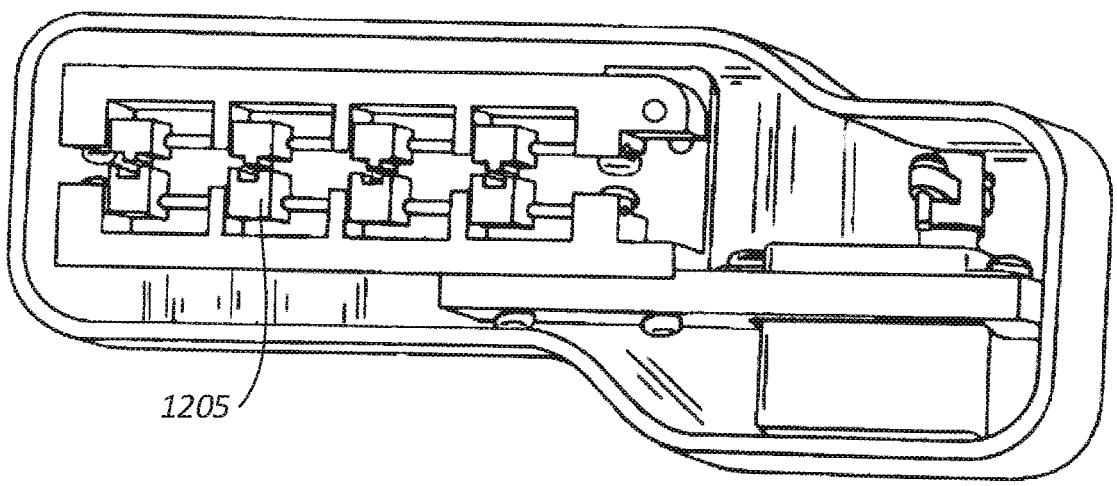
FIG. 12B shows a sectional view though a midline of the controller apparatus shown in FIG. 12A.

FIGS. 12A and 12B illustrate another variation of a controller having four independently operable gripper pairs that may be clamped and locked over a proximal end of a steerable device having four axial translation regions. In FIG. 12A the device includes an upper region that is hinged 1203 to the lower region with four pairs of friction grippers 1205 divided between the upper and lower regions. The friction grippers may be driven by servo motors 1213 to slide the friction grippers on the sliding rails and thereby slide the axial translation region held by a particular pair of friction grippers either proximally or distally to bend the distal bending region. Either or both the upper and lower regions may be enclosed within a housing 1216. FIG. 12B shows a sectional view through the controller shown in FIG. 12A. In this example the friction grippers have a tongue-and-groove design to more securely hold the axial translation regions clamped between them.

Figure 13A:
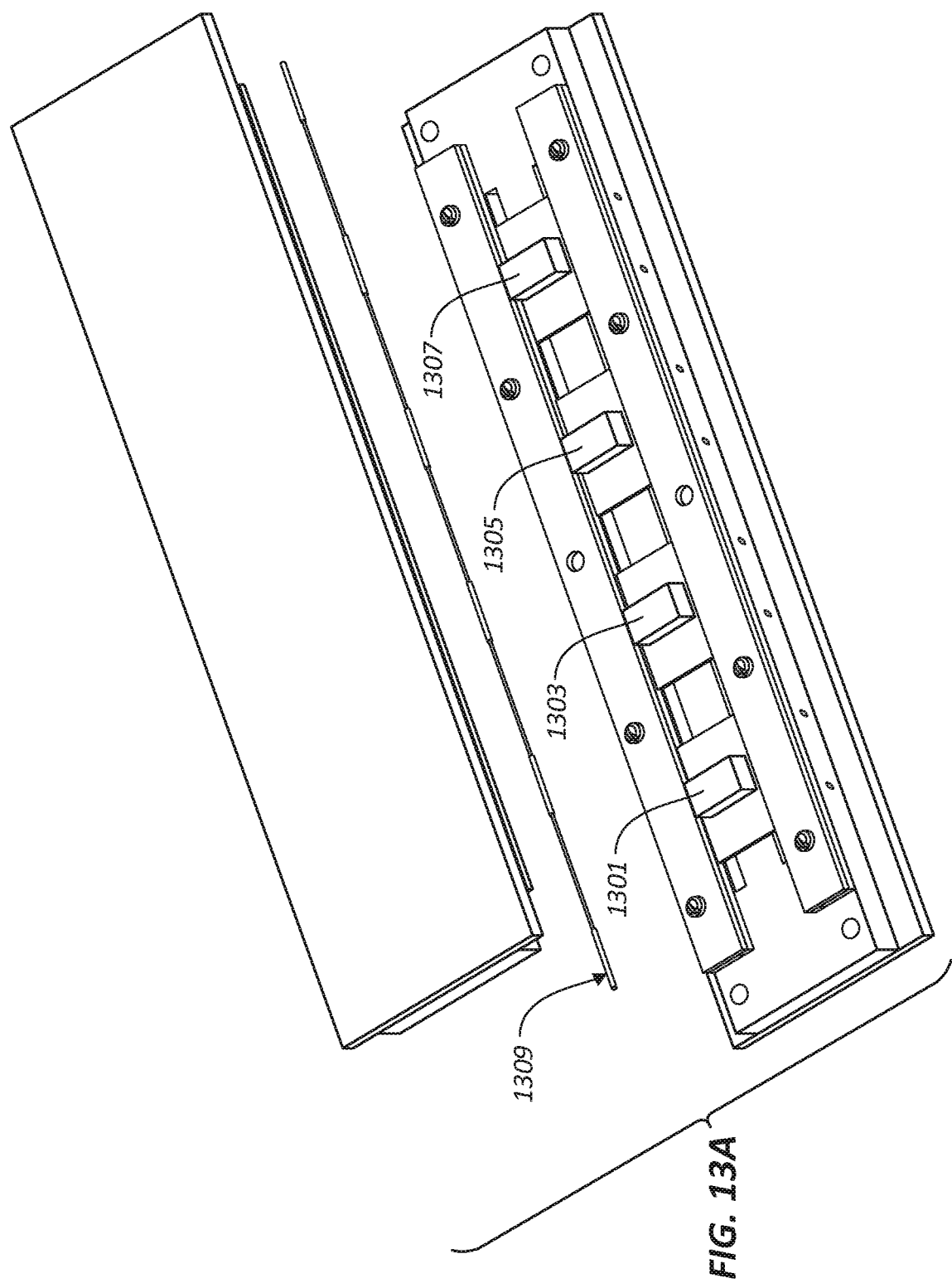
FIG. 13A is an exploded partial view of another variation of a controller apparatus and a proximal end region of a steerable device as described herein, having four in-line axial translation regions each connected to a tendon (not shown) for actuating a distal end of the steerable device. The controller shown in FIG. 13A includes multiple pairs of clamping, gripping surfaces for gripping the axial translation regions; the bottom gripping surfaces are shown and each may be independently actuated.
Figure 13B:
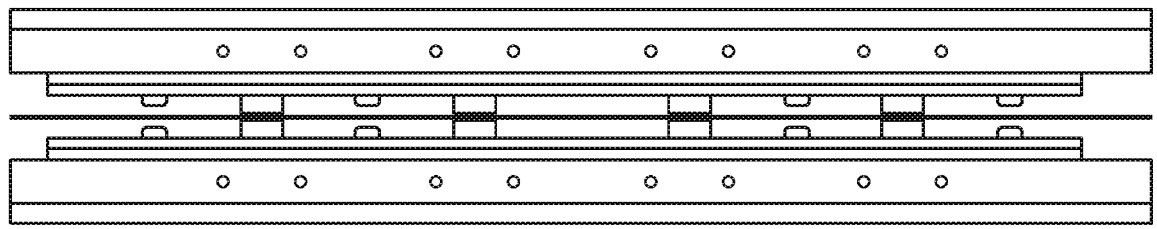
FIG. 13B is a side view of the apparatus of FIG. 13A showing a proximal end region with multiple axial translation regions of a steerable device clamped between pairs of gripping surfaces.
Figure 13C:
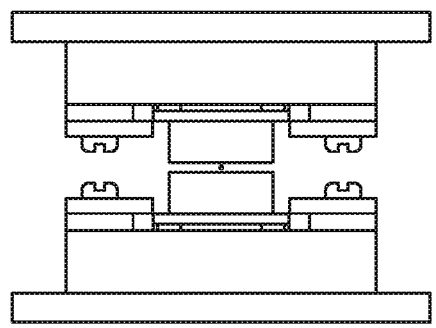
FIG. 13C shows an end view of the apparatus of FIG. 13A.
Figure 13D:
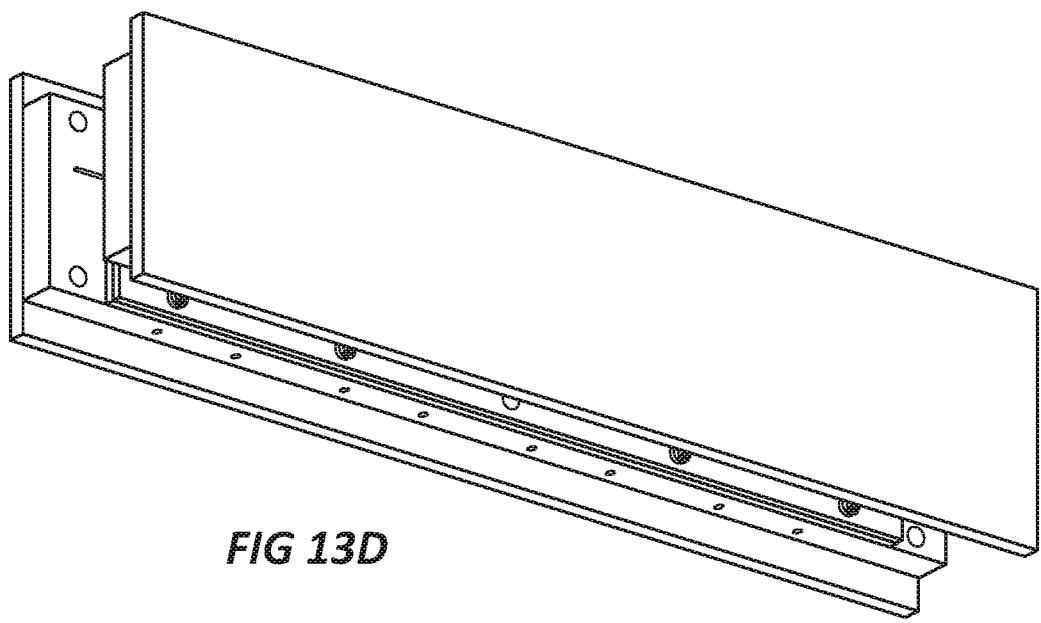
FIG. 13D shows a top perspective view of the apparatus of FIG. 13A.

FIGS. 13A-13D illustrate another variation of a hand controller for controlling bending of a steerable device such as those descried above (e.g., having a plurality of axial translation regions). In FIG. 13A, a partially-exploded view shows an apparatus having four pairs of friction grippers 1301, 1303, 1305, 1307 for securing to the axial translation regions at the proximal end of a device 1309. As in the variation shown in FIG. 12A, the friction gripper may be locked over the device 1309 to secure the axial translation regions and allow them to be individually controlled. This is illustrated in FIG. 13B in a side view and FIG. 13C in an end view. FIG. 13D shows a top perspective view.

In any of these examples, the controller may include a single friction gripper, rather than a pair of friction grippers. For example, a single friction gripper may include a channel that is approximately the same size as the device, and can be formed of a material (e.g., rubber) that can be compressed around the axial translation region of a device to secure it for translation by the gripper region. As mentioned above, the gripper region may grip the axial translation region by mechanical means (e.g., clamping, etc.) or by non-mechanical means (e.g., magnetically, electrostatically, etc.).

Figure 13E:
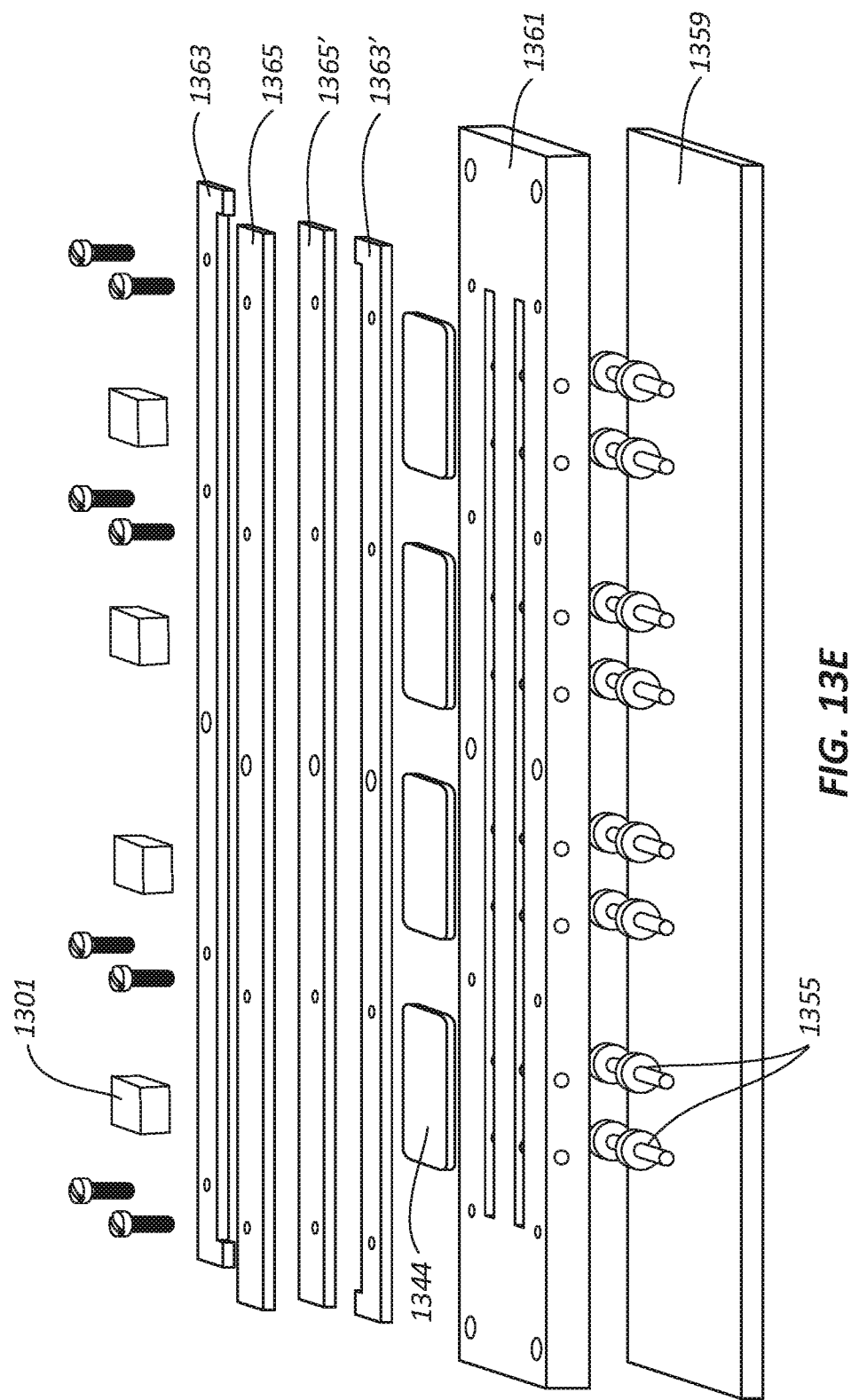
FIG. 13E shows an exploded view of the bottom half of the device shown in FIGS. 13A-13D.

In general, a friction-based gripping system with runners/tracks may be used. In addition, lower running friction controllers may use sliders that run on encapsulated bearings. FIG. 13E shows an exploded view of the bottom half of the controller shown in FIGS. 13A-13D. In this example, a gripper surface 1301 rests on bearings 1355 (shown as pairs of annular bearings connected by a shaft) and sliders 1344. "Grippers" may be mounted on the sliders 1344 (or runners), which are high friction pads. A base 1359, bearing housing 1361, spacers 1365, 1365' and caps 1363, 1363' may be used to secure and partially enclose the sliders and grippers.

In general, the controller may be configured as a single-use, disposable controller or as a multi-use, reusable controller. A single-use, disposable controller may be supplied sterile, and may be sterilized using steam (e.g., autoclave), ethylene oxide, gamma radiation or other means. A multi-use, reusable controller may be re-sterilized between subject cases. Alternatively, the controller may be unsterile and may be used with a sterile sleeve or covering. The sleeve or covering may be a single-use or reusable sleeve or covering.

Described below in reference to FIGS. 18A to 25D are examples of multi-part controllers that may be used across a sterilization barrier. For example a portion of the controller to which the elongate steerable devices such as those described here may be coupled may be separated from the driver assembly, and may be pre-packaged and pre-sterilized as described above, either alone or in combination with the elongate steerable devices described herein (e.g., having axially and sequentially arranged sliding controls at the proximal end for steering a tip region). In some variations, the cartridge portion is then used within the sterile field, while the reusable/durable driver assembly may be used outside of the sterile filed, or encapsulated behind a sterile barrier such as a sleeve, bag, curtain, etc. The two parts (cartridge and driver assembly) may be coupled to each other with the (e.g., unbroken) sterile barrier between the two, yet still align and engage with each other so that the cartridge may be actuated by the driver assembly through the barrier.

As mentioned, in any of the controllers described herein, the controller may be divided up into separate and interacting (interlocking) components such as a cartridge for coupling the elongate steerable device (e.g., guidewire/catheter) to a driver assembly (also referred to as an actuation/control unit subassembly). The driver assembly may be a reusable, non-sterile actuation unit (that may be made sterile by placing a disposable sterile sleeve over it as described above and illustrated herein). The driver assembly may house electronics, motors and bearings, etc. A separate cartridge component may engage with the driver assembly and also couple to and typically grip an elongate steerable device (e.g., guidewire/catheter). This cartridge may be a disposable and sterile cartridge which also couples to the actuation unit to control bending of the tip of the elongate steerable device. FIGS. 18A-25D help illustrate this.

For example, a disposable elongate steerable device may be provided already coupled to a disposable cartridge to facilitate rapid deployment. A user, once the actuation unit is inserted into the sterile sleeve as described above, may connect (e.g., snap) the cartridge onto the actuation unit, and it is ready to steer.

FIG. 18A shows a controller that can be assembled (either using a sterile field or not) by connecting the cartridge 1804 with the driver assembly 1806. In this example, all couplings between the cartridge and the actuation unit are magnetic 1811, so that it may automatically finds its own position alignment relative to the two. Further, the magnetic couplings/connectors could be positioned in a pattern of polarities so that two components can only engage in a predetermined orientation. The couplings could, however, be something other than magnetic to achieve the same result, including, e.g., mechanical couplings such as snaps, clasps, or the like, which may also be oriented and/or arranged to operate only in a particular, predefined orientation. FIG. 18B shows the combined (connected) controller 1800.

Figure 19A:
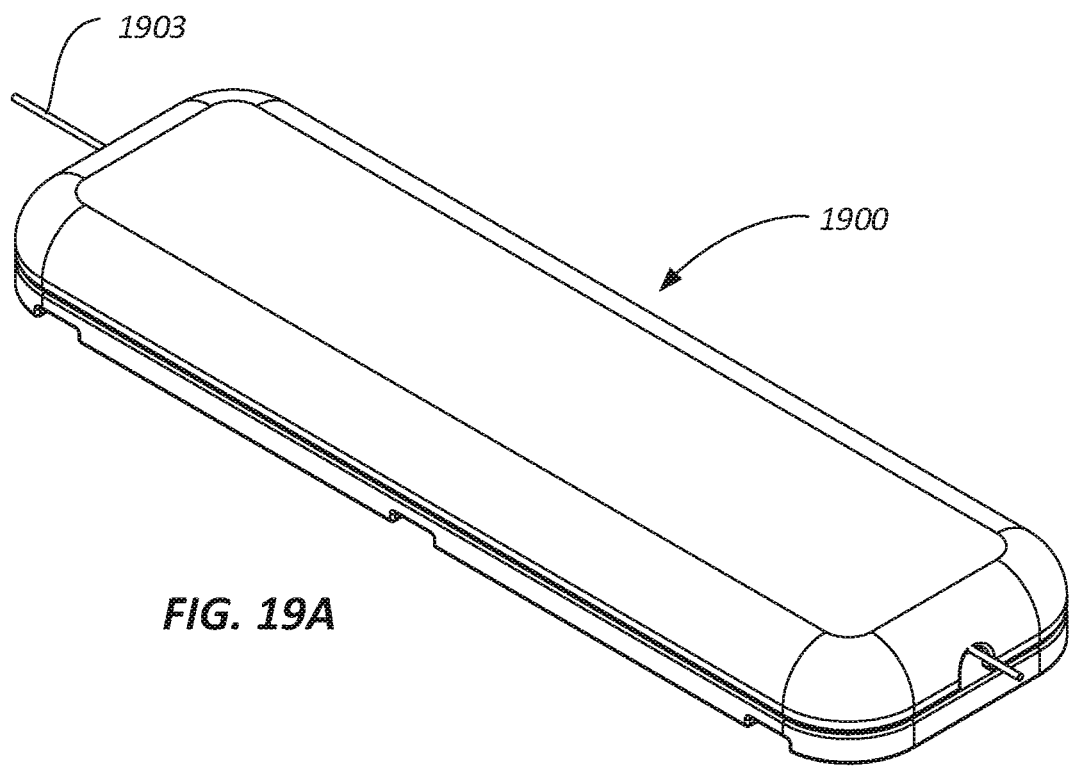
FIG. 19A shows a front perspective view of the cartridge of a multi-part controller, including an elongate steerable device.
Figure 19B:
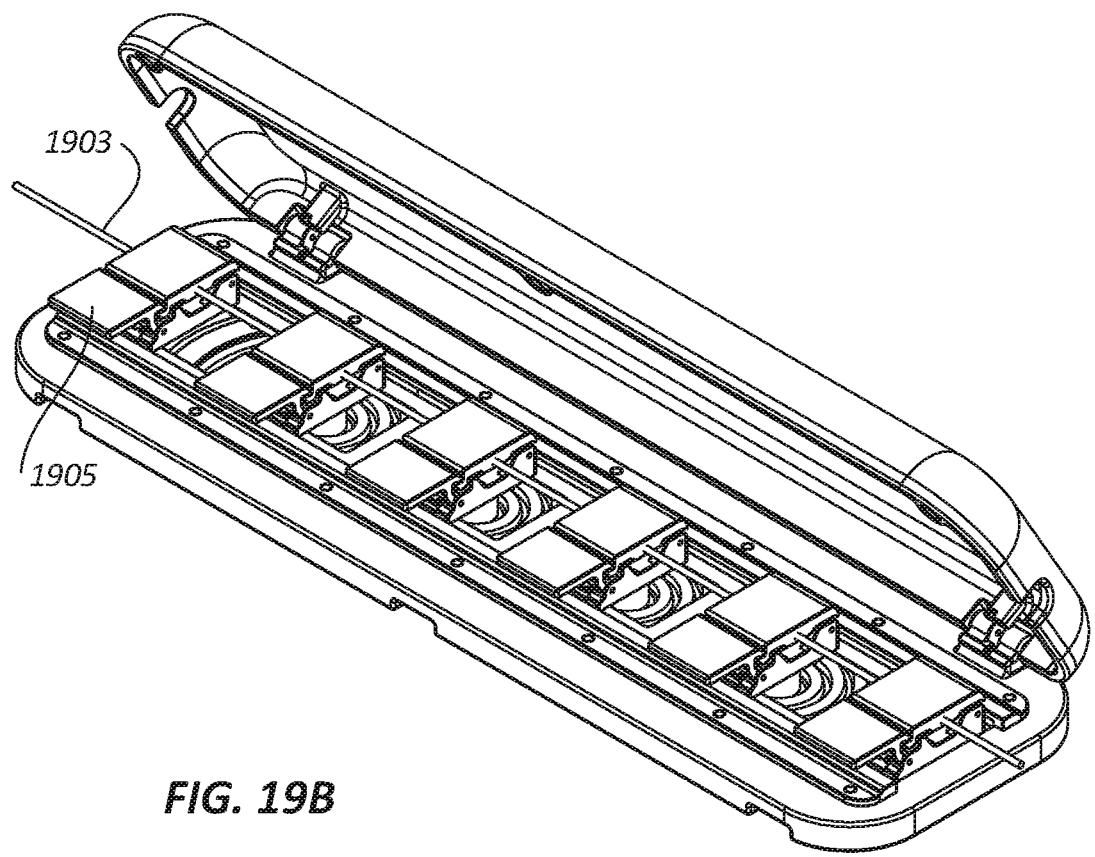
FIG. 19B shows the cartridge of FIG. 19 with a door open to show six friction grippers securing different portions (including sliding elements) of the elongate steerable device.
Figure 19C:
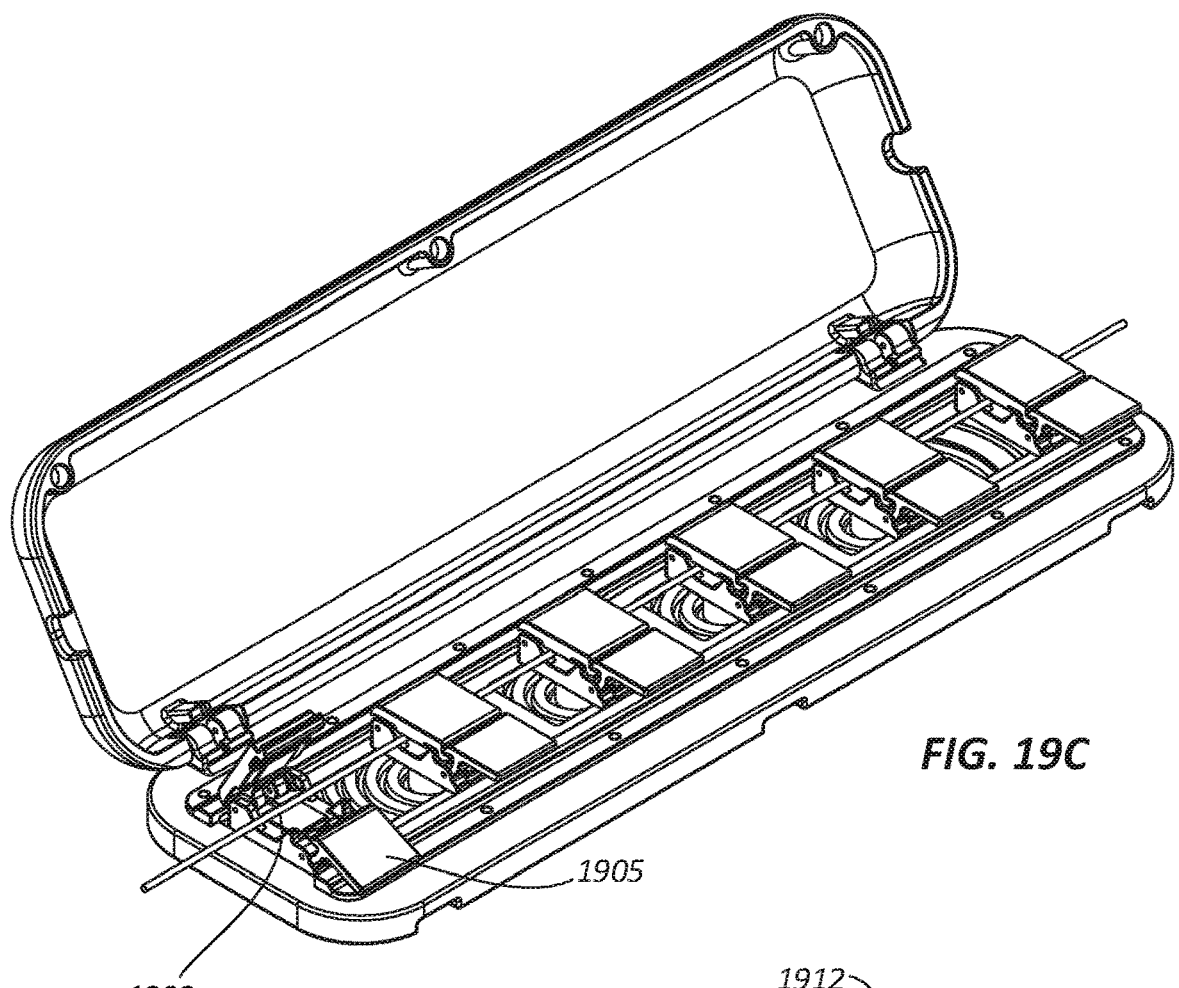
FIG. 19C shows the cartridge of FIGS. 19A and 19B with one of the friction grippers opened, showing a portion of the proximal end of the elongate steerable device.

FIGS. 19A and 19B show front perspective views of one variation of a cartridge 1900 portion of a system that is pre-loaded with an elongate distally steerable device 1903 such as a guidewire/microcatheter as described above. In this example, the device includes a plurality of friction grippers 1905 that are closed (and may be releasably locked) over the elongate steerable device. FIG. 19C shows another example of the cartridge with one of the friction grippers 1905 opened, showing the slider portion 1909 of an elongate steerable device. Any number of friction grippers may be used, typically corresponding to the number (or one or two more than the number) of slider controls controlling the tension wires (tendons) in the device.

Figure 20A:
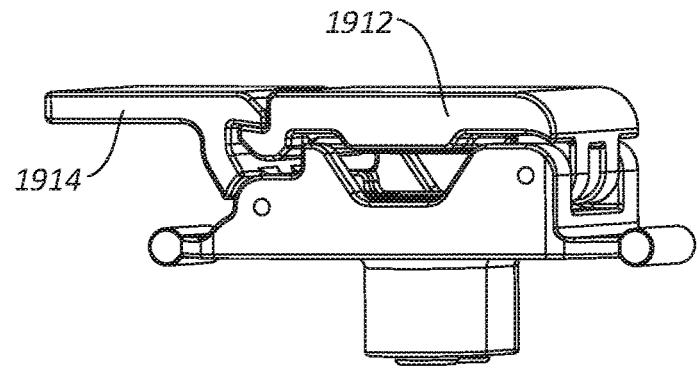
FIGS. 20A and 20B show side perspective and bottom perspective views, respectively, of one example of a friction gripper, as described herein.
Figure 20B:
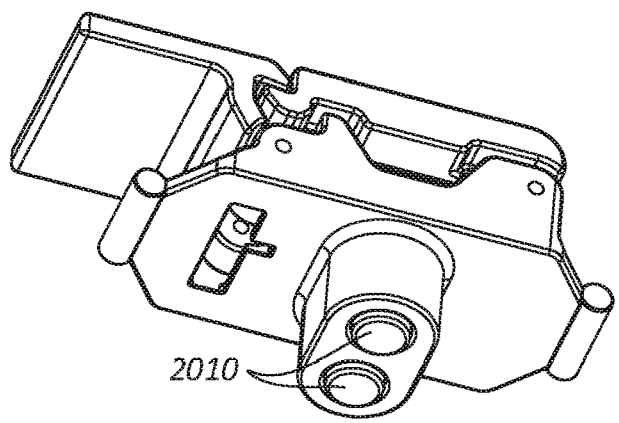

FIGS. 20A and 20B show side perspective and bottom perspective views, respectively of a friction gripper. In general, the friction grippers are mounted to a proximal-to-distal line such as a rail, frame, etc. and allowed to each slide (independently of each other) in the proximal to distal axis. Thus, when they are clamped onto the slider controls of the elongate device, they may be actuated to steer the tip, as described above.

In FIG. 20A, the friction gripper is shown to have a hinged upper friction surface 1912 that clamps down onto a bottom friction surface, forming a pair of friction surfaces. As mentioned above, these friction surfaces may be formed of a material having a high gripping strength to the elongate member. The friction gripper may include a latch, lock or other releasable mechanism 1914 for holding the friction member securely against the slider control. Thus, in this example, each set of grippers has its own spring-loaded hinge and latch system. A guidewire/catheter can be quickly decoupled from the cartridge by opening all of the grippers. It can then be recoupled at will by locating between the grippers, longitudinally aligning the axial translation regions with the friction grippers and closing all the friction grippers. In the example, shown, each set of grippers has high-friction silicone grip pads (not visible in FIG. 19C, 20A-20B) to ensure that the guidewire/catheter does not slip. In addition, as shown in FIG. 20B, each set of grippers may include a coupler 2010 (e.g., magnetic coupler) for engaging a drive member on the driver assembly.

Figure 21A:
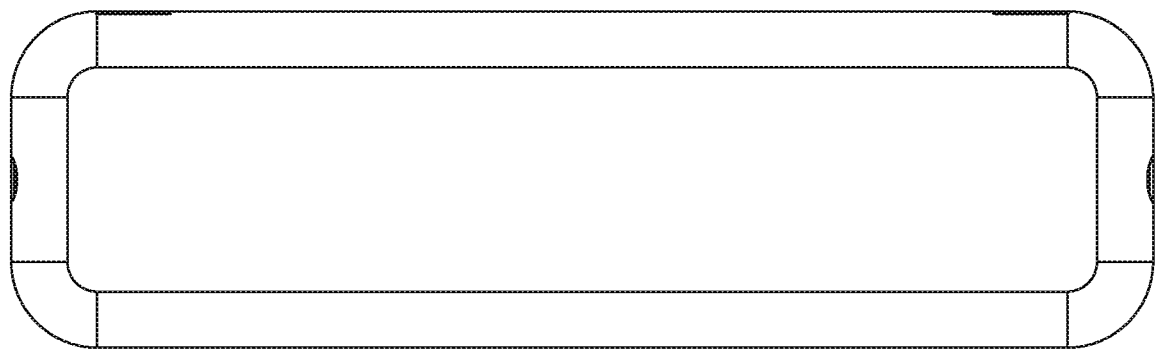
FIGS. 21A, 21B and 21C show top, side and bottom views, respectively, of a cartridge such as the cartridge shown in FIGS. 18A and 19A.
Figure 21B:
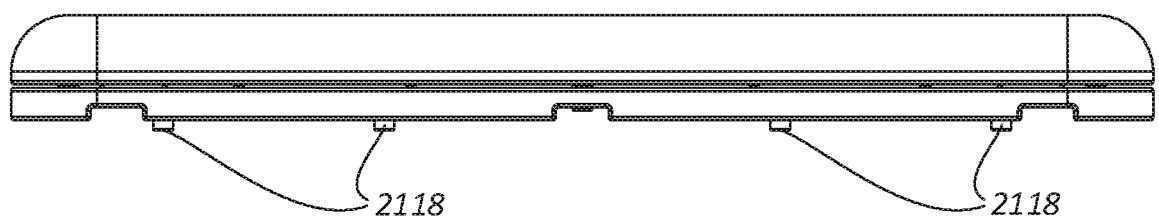
Figure 21C:
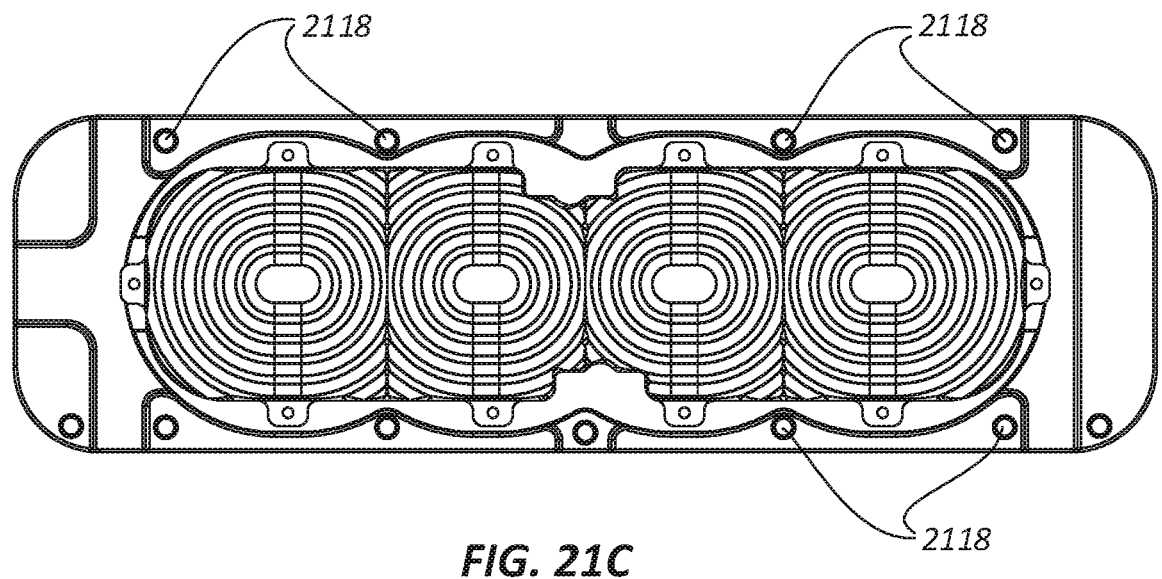

FIGS. 21A to 21C illustrate top, side and bottom views of a cartridge assembly as described above. In this example, coupling member (magnets) 2118 are arranged on the bottom in a pattern (e.g., of location and magnetic polarity) so that it can be aligned with and coupled to the drive members in the drive assembly.

Figure 22:
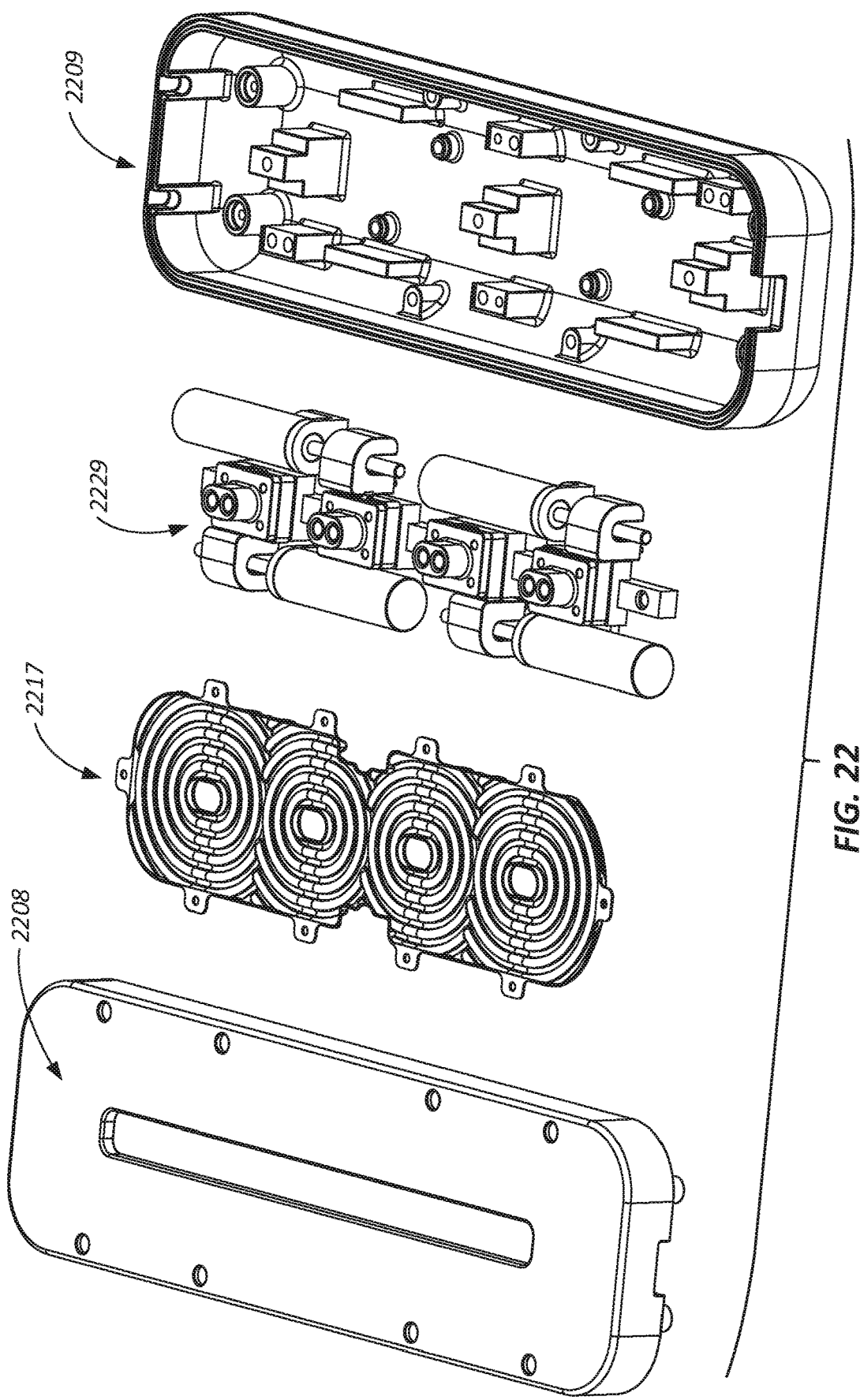
FIG. 22 shows an exploded partial view of a driver assembly such as the one in FIG. 18A. For simplicity, some elements (e.g., power line, wiring, circuitry, screws) have been omitted.

FIG. 22 shows an example of a driver assembly such as the one shown in FIG. 18A, in an exploded view, showing the upper housing 2208, a protective bellows 2217, four drive members 2229, and a bottom housing 2209. Upper housing includes a slot through which the axially (proximal-to-distal axis) moving drive elements may extend. The protective bellows allows the drive members to move axially within the range for actuating the individual tendons when coupled to each of the grippers as described above. For example, the drive members may be configured to each move independently in the axial-to-proximal line +/−1 inch (e.g., +/−0.8 inches, +/−0.5 inches, +/−0.4 inches, +/−0.3 inches, +/−0.1 inches, etc.). The bellows may move with the drive member. In this example, each drive member includes a pair of magnets that are complimentary to the magnets in the grippers of the cartridge so that they may magnetically couple; thus motion of one of the drive member results in motion of the corresponding gripper and therefore actuation of the tendon (push/pull).

Figure 23:
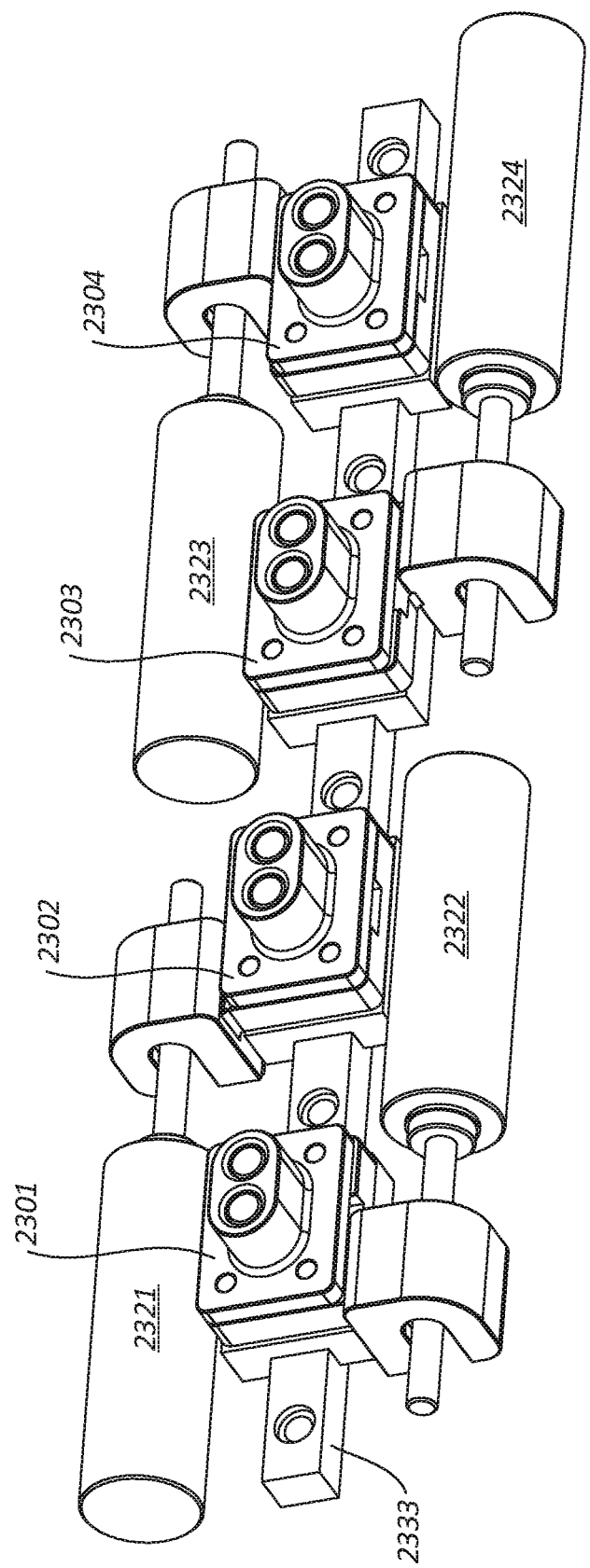
FIG. 23 shows an enlarged view of the drive members of the driver assembly shown in FIG. 22, including four drive members each connected to (and/or including) a driver, driving motion of the drive member (each with a magnetic coupler) in the proximal to distal axis.
Figure 24A:
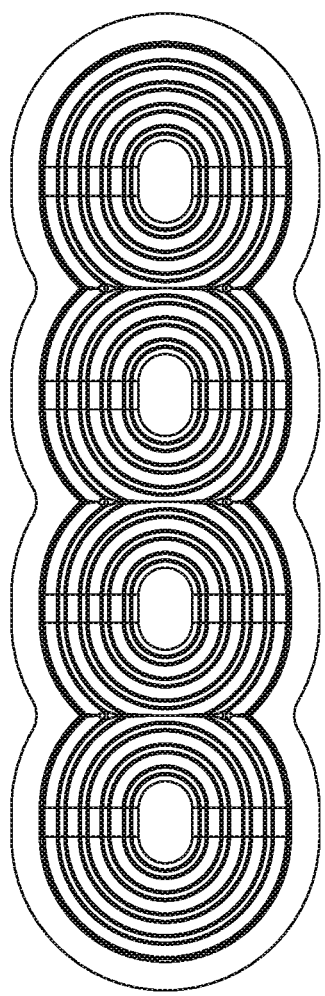
FIGS. 24A-24B show top views of a driver assembly of a controller.
Figure 24B:
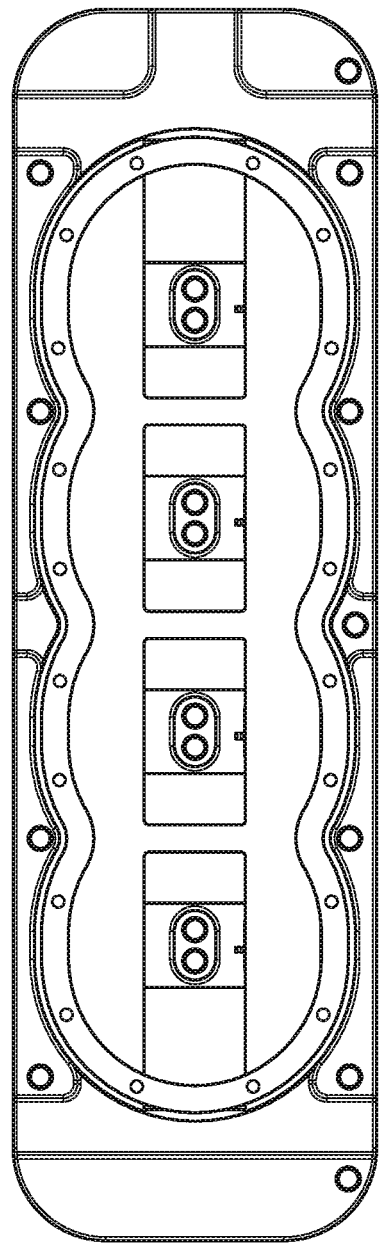

FIG. 23 shows an enlarged view of the four drive members 2301, 2302, 2303, 2304, and each drive member includes and/or is connected to a dedicated driver (motor) 2321, 2322, 2323, 2324. Each drive member is also connected to a track, rail, gantry, or the like allowing axial (distal to proximal) sliding. In FIG. 23, there is a common linear rail 2333 (with ball bearings, not shown). The drivers in this example are four DC motors, each with a position encoder for accurate position feedback and control. The driver assembly may also include four motor drivers (e.g., underneath the linear rail 2333) and four limit switches (not visible) for position calibration on startup. The grippers are actuated via the movement of the drive members, (e.g., lead screws on the motors) which drive the linear stages of the drive members that are magnetically coupled to the grippers when the cartridge is attached. FIG. 24A shows another view of the protective bellows and FIG. 24B shows a top view of the drive assembly with the bellows removed.

Figure 25C:
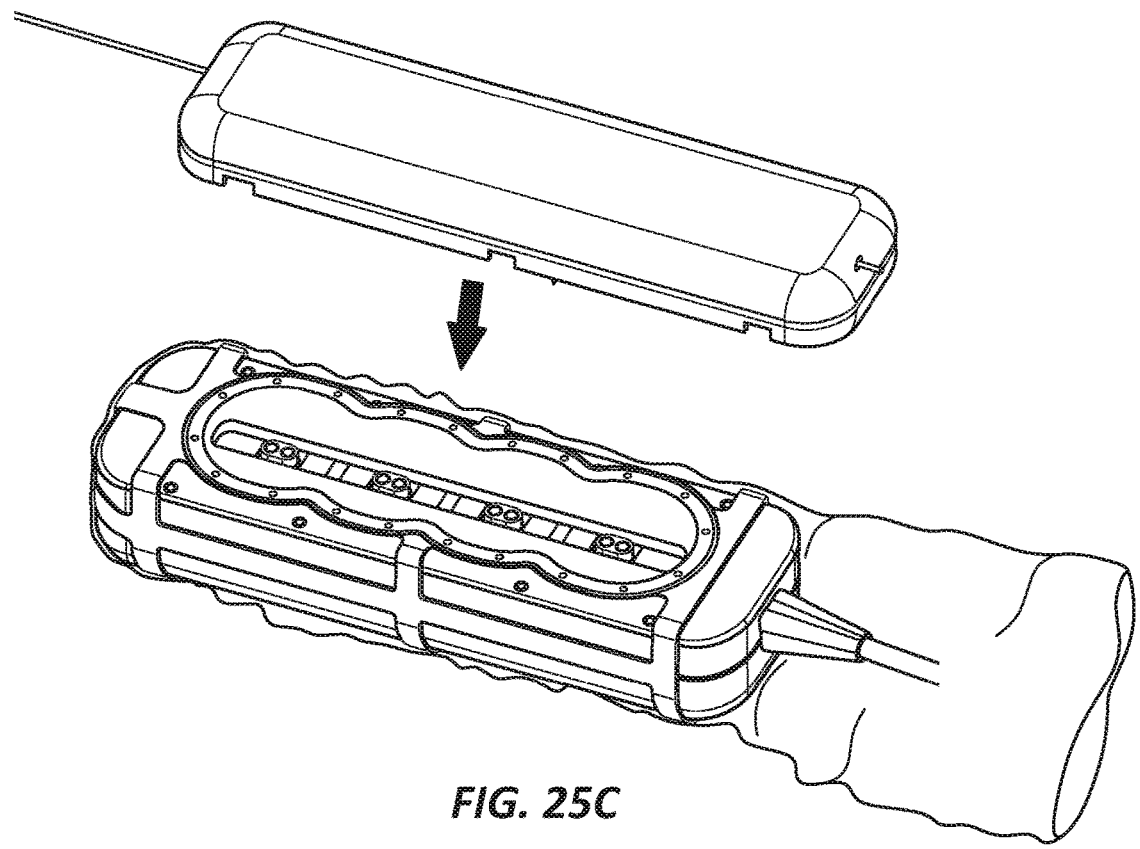
FIG. 25C illustrates the attachment of the cartridge (including an elongate steerable member) onto the covered driver assembly to form the complete controller as shown in FIG. 25D.
Figure 25D:
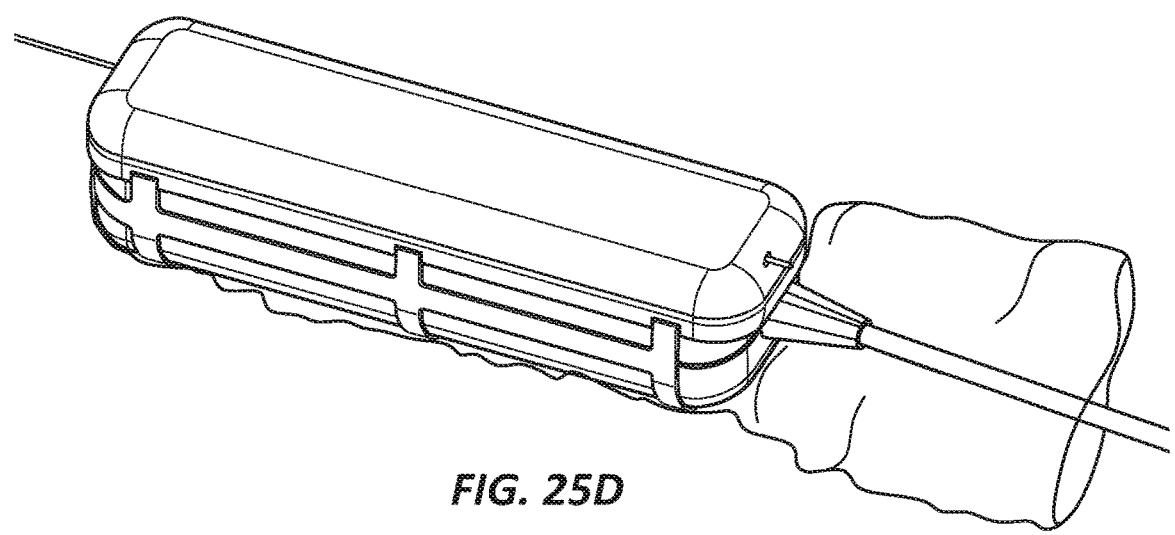
FIG. 25A shows a side perspective view of one variation of a sterile cover.
FIG. 25B illustrates insertion of a (reusable) driver assembly portion of a controller into the sterile cover of FIG. 25A.

As mentioned above, any of these apparatuses may be used with (and may include or be packaged with) a sterile barrier. For example, the reusable driver assembly portion of the controller may be non-sterile but may be held within a sterile field by enclosing it within a sterile barrier such as a sterile sleeve. This may make the actuation/controller unit sterile while in use. For example, FIG. 25A illustrates one variation of a (e.g., disposable) sterile sleeve 2505. This example also includes a frame or cage 2507 within the sterile sleeve to hold the driver assembly in a fixed position while within the sterile sleeve. For simplicity, the sleeve shown in FIGS. 25A-25D is short, but it may be any length. In FIG. 25A, the cage is joined to a standard sterile sleeve, and a flexible silicone membrane at the top region allows the actuator-gripper couplers to move freely. As illustrated in FIG. 25B, the actuation unit slides smoothly into the cage and once inside is completely sealed from the sterile field. Once the sleeve is over the actuation unit, the cartridge can then be coupled on top, as illustrated in FIGS. 25C and 25D.

In any of these examples where energy is used to actuate and control the controller, the controller may be actuated and controlled via connecting wires or wirelessly. A wireless controller may include an onboard battery pack. In some variations, the controller may be connected to wall power (as shown in the example of FIG. 18A, which includes cord 1844).

The devices described herein may have many advantages over existing guidewires and catheters, including other steerable and/or very thin (small OD) devices. For example, these devices may use very few parts. In particular, these devices typically have a single lumen for the tension wires (where many others have multiple lumens) and may control the spatial positioning of the wires within the distal end using a flexible core that is highly flexible (either via the use of a polymer, or a multi-part design, or both). This may allow the tip to deflect under the influence of the forces that can be applied. The tension wires may have any appropriate diameter. For example, a tension wire may have a diameter of between about 0.03 mm to 0.05 mm. However, this may limit how much tension the tendons can withstand. If the distal core comprised a single part metallic construct, as disclosed in other devices, the tension wires would break before the tip deflected sufficiently. Thus, the core regions described herein are not only flexible, but also control the spatial positioning of the tension wires. The "spinal" cores described herein may use interchanging, highly flexible bending regions with small, square/round cross-sections, and also stiffer placeholder regions (with "cross" or "plus-sign" cross-sections). A similar multi-part core could also be used.

The proximal connector devices described herein for steering the devices also offer numerous advantageous. For example, because of the proximal actuation region (including the axial translation regions), any of the devices described herein may easily and readily allow passage of things over/through the guidewire/catheter. The connectors may therefore easily and quickly attach to the outer surface of the proximal end and actuate and deflect the tip, but can be rapidly removed and preserve the inner and outer diameters of the guidewire/catheter devices. This is in contrast to other steerable catheter systems and controls which may have a large permanent control unit mounted to the outside of the catheter, which may preserve the inner diameter of the catheter, but it does not allow large catheters/introducers to be passed over the outside.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An elongate steerable device for insertion into a subject's body, the device extending from a bendable distal tip region to a proximal handle region, the device comprising:
    a plurality of tendons, wherein each tendon of the plurality of tendons is attached to the distal tip region and extends from the distal tip region to the proximal handle region; and
    a plurality of axial translation regions sequentially arranged along an outer surface of the proximal handle region, wherein each axial translation region of the plurality of axial translation regions is coupled to a tendon of the plurality of tendons;
    wherein each axial translation region is configured to move in a proximal to distal line to axially translate the tendon coupled to the axial translation region and thereby deflect the distal tip;
    wherein the axial translation regions are configured to allow passage of a vascular catheter over the axial translation regions.

2. The device of claim 1, wherein the axial translation regions are elastically connected to each other.

3. The device of claim 1, wherein the axial translation regions are connected to a core within the proximal handle region.

4. The device of claim 1, wherein the device is configured as a guidewire.

5. The device of claim 1, wherein the device is configured as a catheter having a central lumen extending therethrough.

6. The device of claim 1, wherein the axial translation regions comprise cylindrical regions that are adjacently arranged along the outer surface of the proximal handle region.

7. The device of claim 1, wherein each tendon of the plurality of tendons is attached to the distal tip region at radially offset attachment sites.

8. The device of claim 1 wherein the tendon comprises a multi-filament wire.

9. The device of claim 1, further comprising an elongate body including the bendable distal tip region, an intermediate region and the proximal handle region.

10. The device of claim 1, further comprising an elongate body including the bendable distal tip region, an intermediate region and the proximal handle region, wherein the elongate body comprises a hypotube.

11. A method of steering an elongate device having a plurality of tendons, wherein each tendon is coupled at a distal end of the device to a distal tip region and each tendon is coupled to a separate axial translation region at a proximal end of the device, and wherein the axial translation regions are arranged in a proximal to distal line along a proximal handle region of the device, the method comprising:
    separately holding at least a first one and a second one of the axial translation regions;
    sliding the first one of the axial translation regions proximally or distally relative to the second one of the axial translation regions to increase or decrease the distance between the first one and the second one, to axially translate the tendon that is coupled with the first one to deflect the distal tip region; and
    passing a vascular catheter over the axial translation regions.

12. The method of claim 11, further comprising inserting the device into a subject's body.

13. The method of claim 11, wherein separately holding comprises frictionally securing each of the axial translation regions to a separate gripper of an actuator.

14. The method of claim 11, further comprising holding a portion of the device that is distal or proximal to the proximal handle region while sliding the first one of the axial translation regions so that the first one of the axial translation regions slides relative to the portion of the device that is distal, proximal or distal and proximal to the proximal handle region.

15. The method of claim 11, wherein separately holding comprises holding the first one of the axial translation regions in a first grip and holding the second one of the axial translation regions in a second grip.

16. The method of claim 11, wherein separately holding each of the axial translation regions comprises holding each of the axial translation regions in separate frictional grips that are independently movable relative to each other.

17. The method of claim 11, wherein separately holding each of the axial translation regions comprises holding either or both a portion of the device that is distal to the proximal handle region and/or a portion of the device that is distal to the axial translation regions.

* * * * *